UNITED STATES PATENT

(12) United States Patent
Newby et al.

(10) Patent No.: US 6,984,223 B2
(45) Date of Patent: Jan. 10, 2006

(54) NEEDLE SAFETY DEVICE

(75) Inventors: C. Mark Newby, Tuxedo, NY (US); Michael Bennett, Summit, NJ (US); Hugh T. Conway, Verona, NJ (US); Bradley M. Wilkinson, North Haledon, NJ (US); John Hitchings, Kinnelon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 552 days.

(21) Appl. No.: 10/165,407

(22) Filed: Jun. 7, 2002

(65) Prior Publication Data
US 2003/0093009 A1  May 15, 2003

Related U.S. Application Data

(60) Provisional application No. 60/354,202, filed on Nov. 13, 2001.

(51) Int. Cl.
*A61M 5/00* (2006.01)

(52) U.S. Cl. ...................... 604/263; 604/110

(58) Field of Classification Search ............. 604/110, 604/198, 263, 192, 187, 136
See application file for complete search history.

(56) References Cited

U.S. PATENT DOCUMENTS

| | | | |
|---|---|---|---|
| 3,463,152 A | 8/1969 | Sorenson | |
| 3,572,334 A | 3/1971 | Petterson | |
| 3,595,230 A | 7/1971 | Suyeoka et al. | |
| 3,827,434 A | 8/1974 | Thompson et al. | |
| 4,160,450 A | 7/1979 | Doherty | |
| 4,170,993 A | 10/1979 | Alvarez | |
| 4,354,491 A | 10/1982 | Marbry | |
| 4,377,165 A | 3/1983 | Luther et al. | |
| 4,676,783 A | 6/1987 | Jagger et al. | |
| 4,681,567 A | 7/1987 | Masters et al. | |
| 4,723,943 A | 2/1988 | Spencer | |
| 4,747,831 A | 5/1988 | Kulli | |
| 4,781,692 A | 11/1988 | Jagger et al. | |
| 4,804,372 A | 2/1989 | Laico et al. | |
| 4,826,490 A | 5/1989 | Byrne et al. | |
| 4,867,746 A | 9/1989 | Dufresne | |
| 4,884,560 A | 12/1989 | Kuracina | |
| 4,887,998 A | 12/1989 | Martin et al. | |
| 4,917,669 A | 4/1990 | Bonaldo | |
| 4,941,881 A | 7/1990 | Masters et al. | |

(Continued)

FOREIGN PATENT DOCUMENTS

EP   0 268 445   5/1988

(Continued)

*Primary Examiner*—Sharon Kennedy
(74) *Attorney, Agent, or Firm*—Gerald Hespos, Esq.; Mark Lindsey

(57) ABSTRACT

A needle assembly includes a needle and a hub mounted to each other. The hub includes a sidewall spaced outwardly from the needle cannula and extending to a distal position between the opposed ends of the needle cannula. A housing integral with the hub defines a sidewall to partially confine a safety shield. The safety shield is slidably disposed about the needle cannula and releasably retained in a proximal position and can be moved to a distal position where the safety shield completely surrounds that portion of the needle hub projecting distally from the hub. The needle assembly includes a spring for propelling the safety shield to the distal position and a latch for releasing the safety shield from the proximal position. The latch may be passively activated by normal usage of the medical implement to which the needle assembly is mounted or alternately activated manually.

28 Claims, 24 Drawing Sheets

U.S. PATENT DOCUMENTS

| | | |
|---|---|---|
| 4,946,446 A | 8/1990 | Vadher |
| 4,969,876 A | 11/1990 | Patterson |
| 4,998,922 A | 3/1991 | Kuracina et al. |
| 5,084,030 A | 1/1992 | Byrne et al. |
| 5,088,986 A | 2/1992 | Nusbaum |
| 5,112,311 A | 5/1992 | Utterberg et al. |
| 5,120,320 A | 6/1992 | Fayngold |
| 5,185,006 A | 2/1993 | Williamitis et al. |
| 5,192,275 A | 3/1993 | Burns |
| 5,219,333 A | 6/1993 | Sagstetter et al. |
| 5,222,945 A | 6/1993 | Basnight |
| 5,246,428 A | 9/1993 | Falknor |
| 5,254,099 A | 10/1993 | Kuracina et al. |
| 5,261,880 A | 11/1993 | Streck et al. |
| 5,266,072 A | 11/1993 | Utterberg et al. |
| 5,269,765 A | 12/1993 | Kuracina |
| 5,295,975 A | 3/1994 | Lockwood, Jr. |
| 5,300,039 A | 4/1994 | Poulsen |
| 5,304,137 A | 4/1994 | Fluke |
| 5,389,085 A | 2/1995 | D'Alessio et al. |
| 5,411,487 A | 5/1995 | Castagna |
| 5,472,430 A | 12/1995 | Vaillancourt et al. |
| 5,484,421 A | 1/1996 | Smocer |
| 5,527,294 A | 6/1996 | Weatherford et al. |
| 5,536,257 A | 7/1996 | Byrne et al. |
| 5,549,558 A | 8/1996 | Martin |
| 5,549,572 A | 8/1996 | Byrne et al. |
| 5,562,624 A | 10/1996 | Righi et al. |
| 5,582,597 A | 12/1996 | Brimhall et al. |
| 5,601,535 A | 2/1997 | Byrne et al. |
| 5,616,135 A | 4/1997 | Thorne et al. |
| 5,718,239 A | 2/1998 | Newby et al. |
| 5,800,404 A | 9/1998 | Poulsen |
| 5,893,845 A | 4/1999 | Newby et al. |
| 6,261,265 B1 | 7/2001 | Mosseri |

FOREIGN PATENT DOCUMENTS

| | | |
|---|---|---|
| EP | 0 286 922 | 10/1988 |
| EP | 0 299 287 | 1/1989 |
| EP | 0 680 767 | 11/1995 |
| GB | 2 202 747 | 10/1988 |
| WO | WO 89/00865 | 2/1989 |

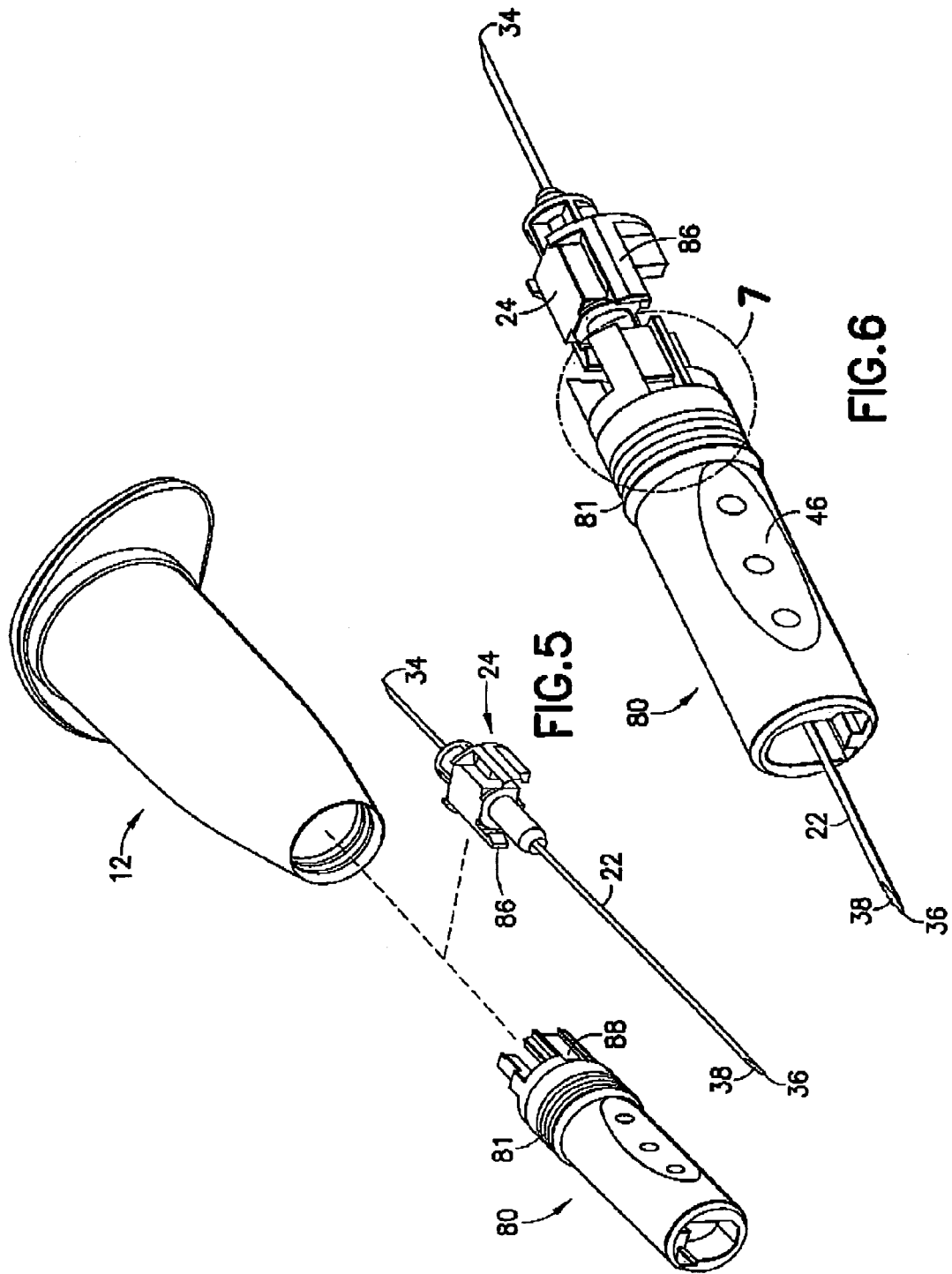

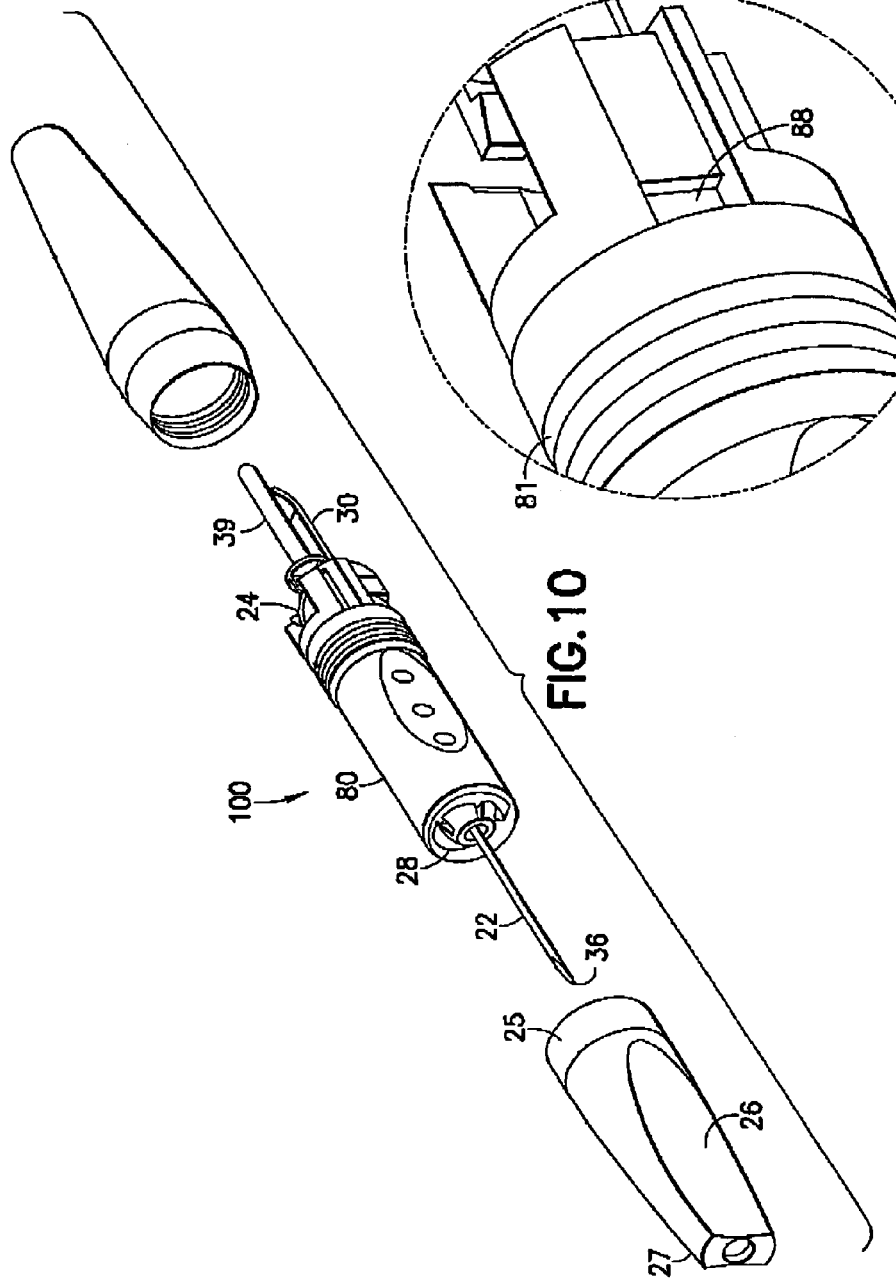

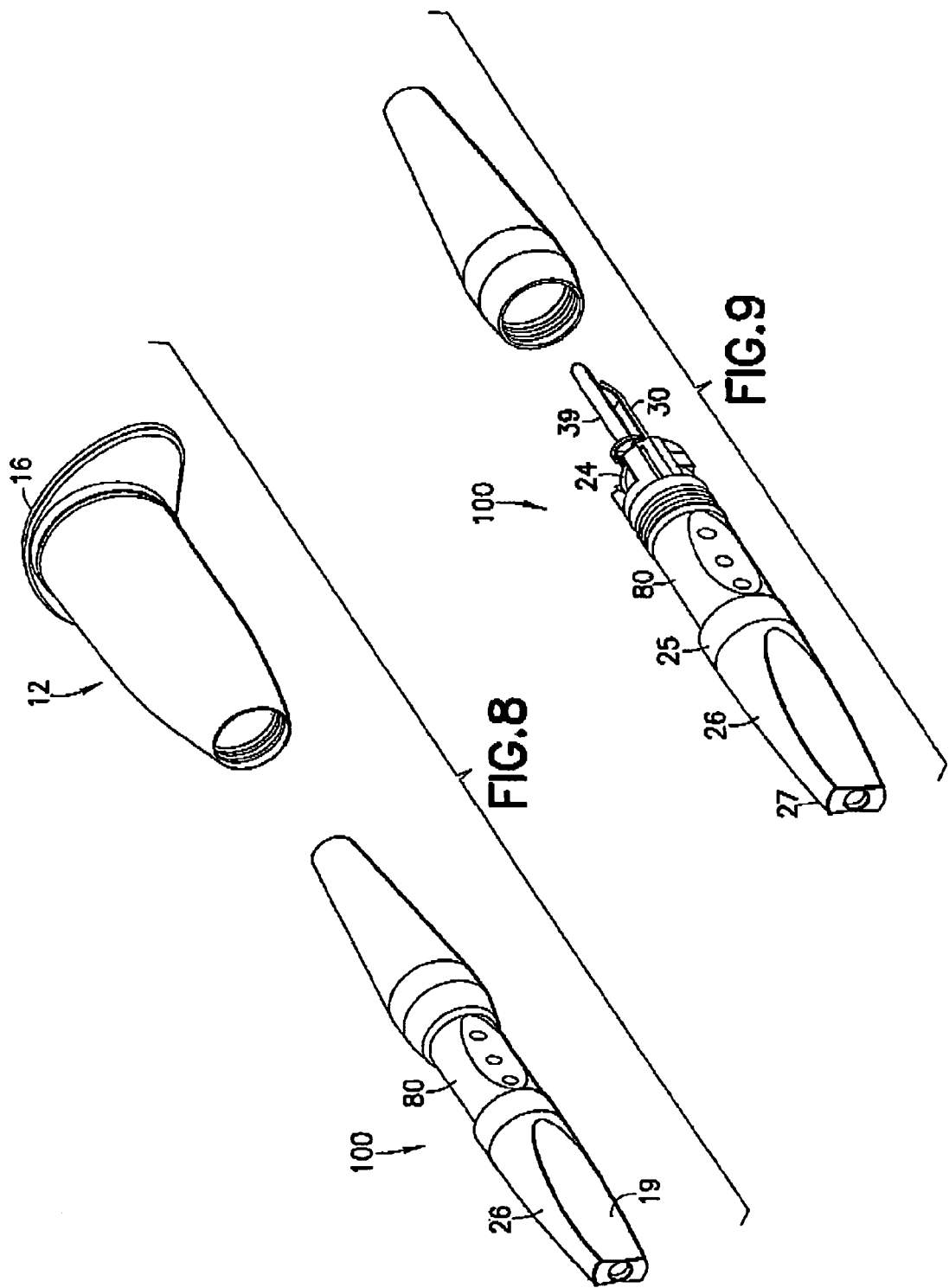

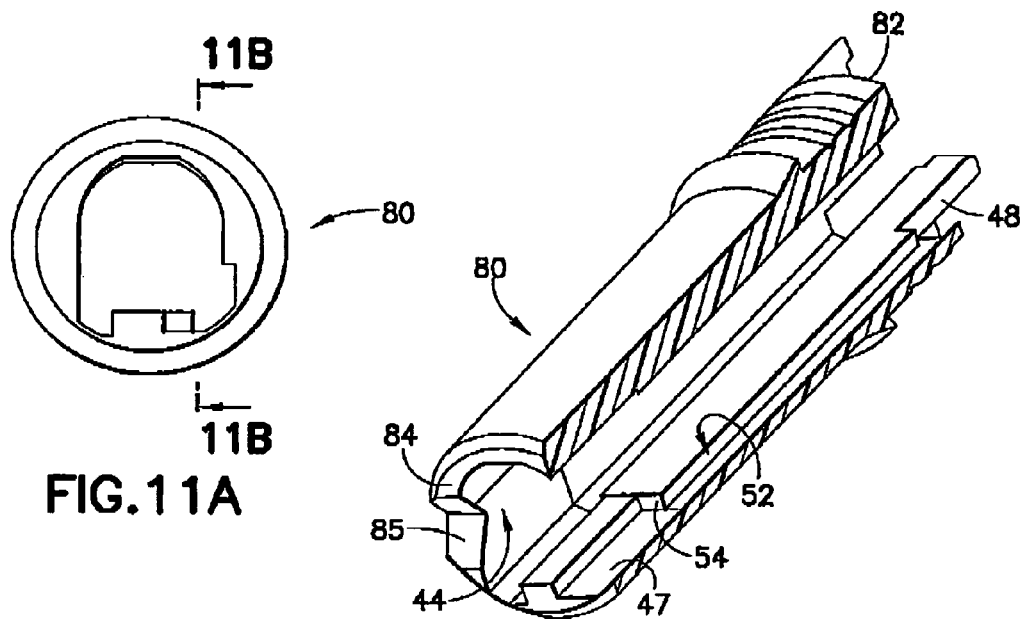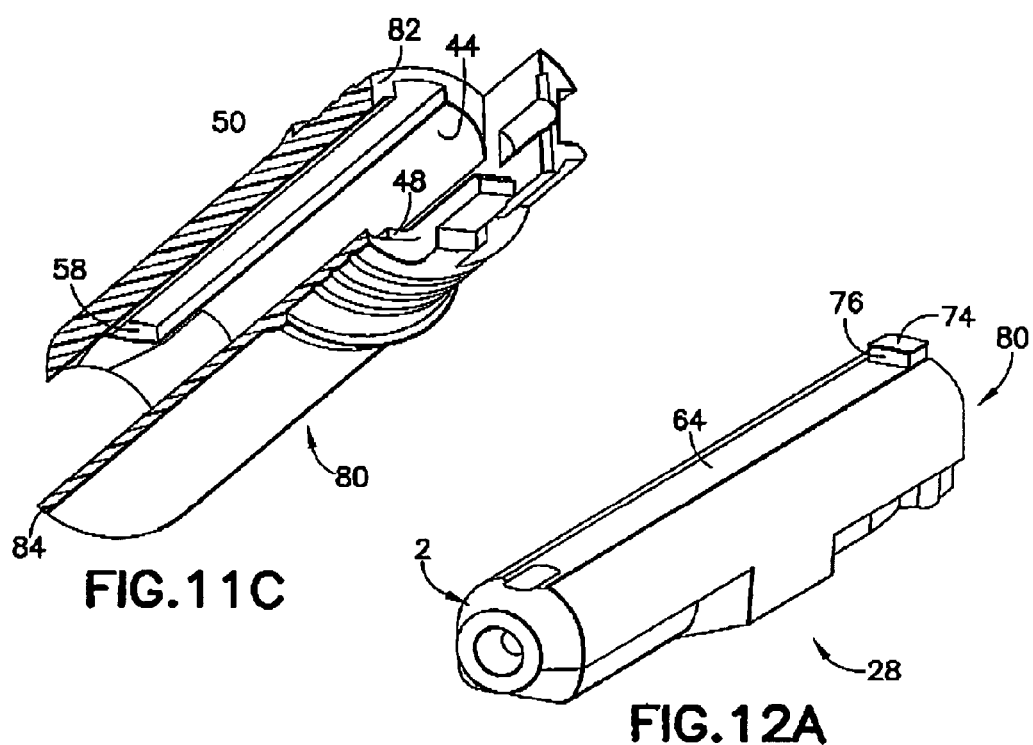

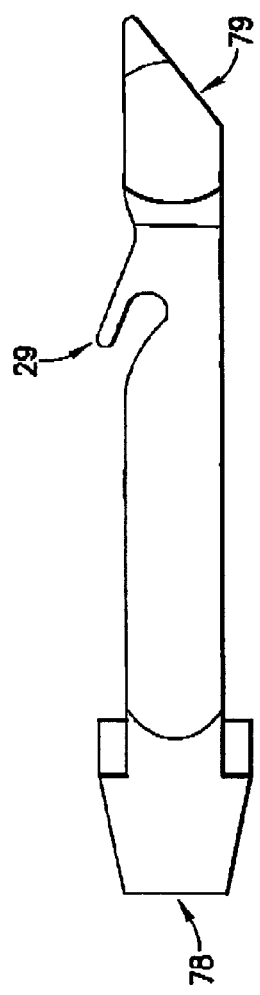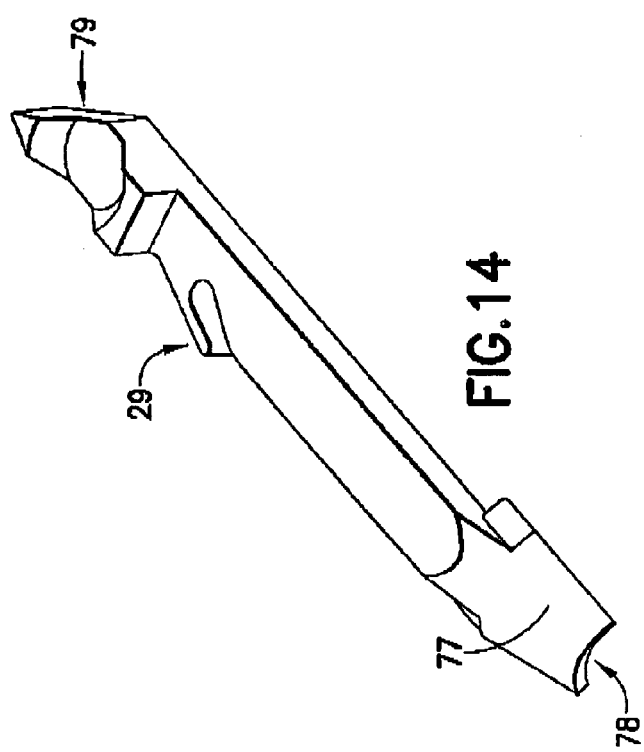

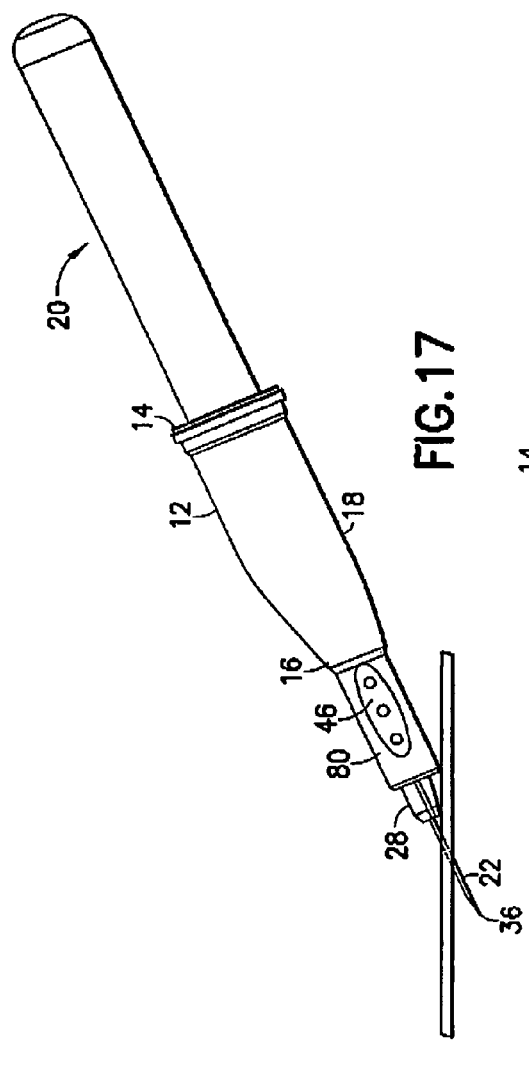
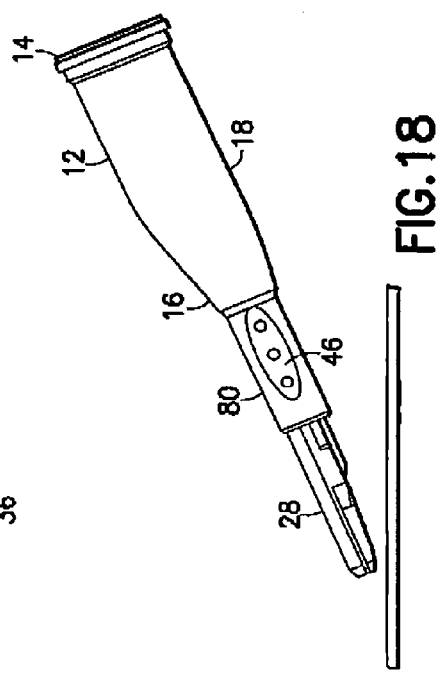

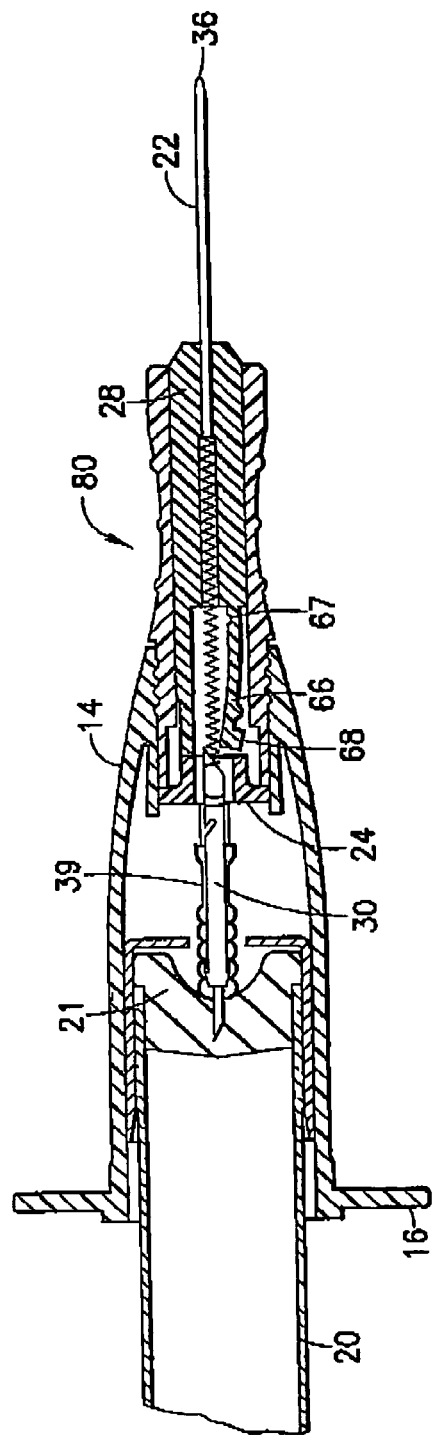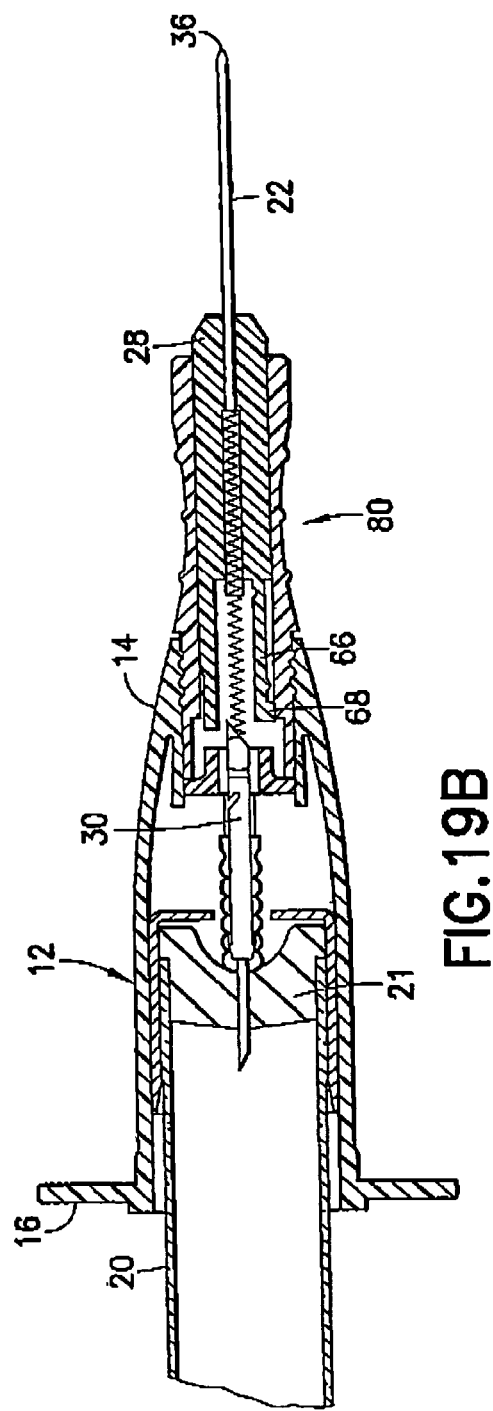
FIG.19A
FIG.19B

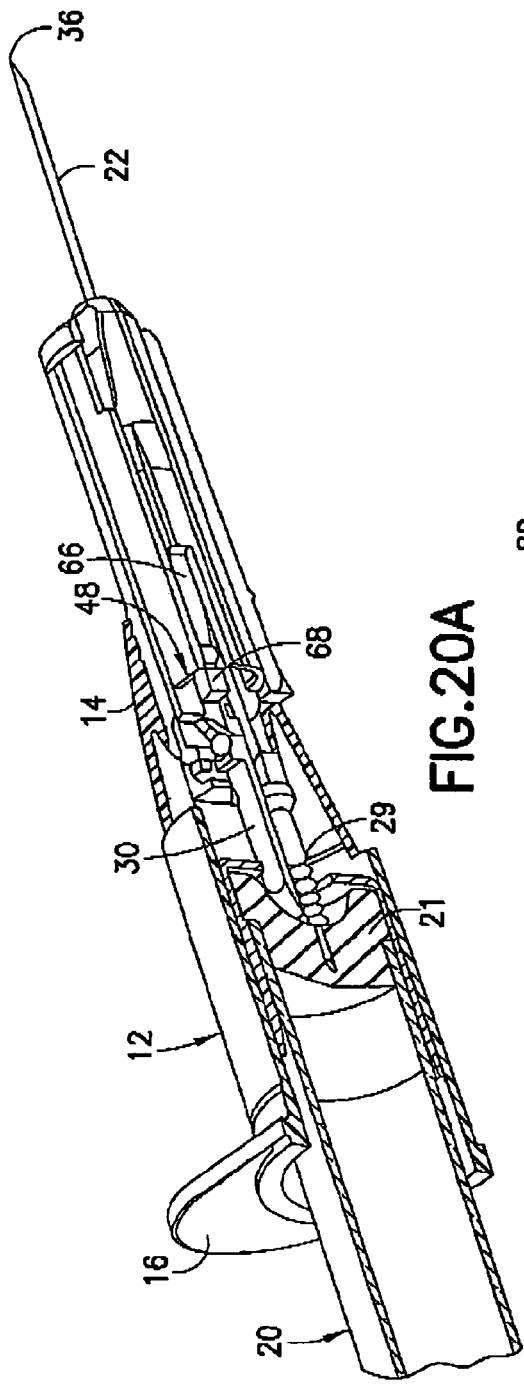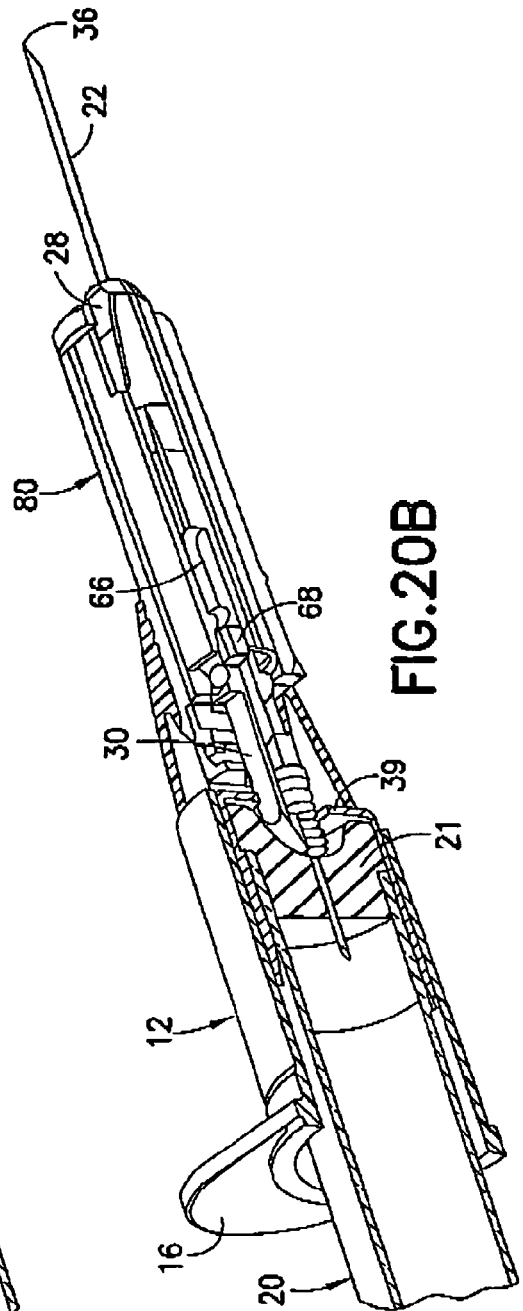

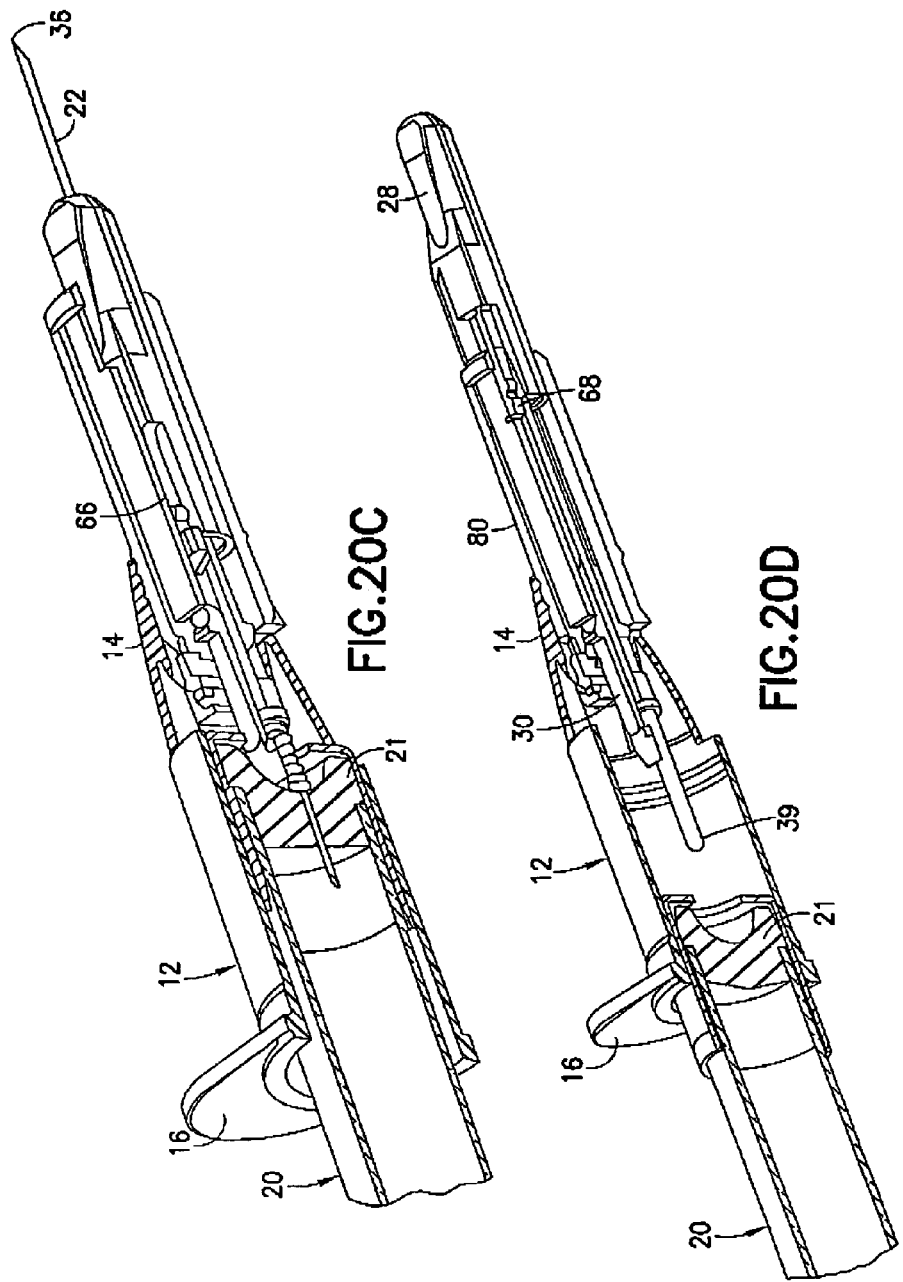

NEEDLE SAFETY DEVICE

RELATED APPLICATION

This application is a non-provisional of U.S. Provisional Patent Appl. No. 60/354,202, filed Nov. 13, 2001.

BACKGROUND OF THE INVENTION

1. Field of the Invention

The present invention relates to a needle assembly having a needle cannula, a hub to which the needle cannula is mounted and a safety shield that can be telescoped from a proximal position where the needle cannula is exposed to a distal position where the needle cannula is safely shielded.

2. Description of the Related Art

A typical needle assembly includes a needle cannula having a proximal end, a pointed distal end and a lumen extending between the ends. A thermoplastic hub is mounted securely to the needle cannula at a location spaced from the distal end. The hub is provided with external threads or other surface configurations for removably mounting the prior art needle cannula on another structure. Some needle assemblies are used for drawing a sample of blood or other body fluid from a patient. The needle cannulas for these assemblies typically have pointed proximal and distal ends, and the needle hub is mounted to a location between the opposed ends of the needle cannula.

A needle assembly that is used to draw a sample of blood or other bodily fluid typically is used with a needle holder. The needle holder has a substantially tubular sidewall with a widely opened proximal end and a partly closed distal end. The hub of the prior art needle assembly can be engaged releasably with the partly closed distal end of the needle holder. Thus, the pointed proximal end of the needle cannula projects into the needle holder, while the pointed distal end of the needle cannula projects distally beyond the needle holder.

The combination of a needle assembly and a needle holder is used with an evacuated tube for drawing a sample of blood or other bodily fluid from a patient. The tube has a closed end, an open end, and a sidewall extending between the ends. The tube is evacuated, and the open end is sealed by a septum that retains the vacuum within the tube. The evacuated tube is dimensioned to be slid into the open proximal end of the needle holder. Sufficient sliding of the evacuated tube into the needle holder causes the proximal point of the needle cannula to pierce the septum of the evacuated tube. Thus, the needle cannula can be placed in communication with the interior of the evacuated tube.

The combination of a needle assembly, a needle holder and an evacuated tube is employed by initially urging the pointed distal end of the needle cannula into a blood vessel of a patient. Once the targeted blood vessel has been reached, the evacuated tube is urged into the needle holder so that the proximal point of the needle cannula pierces the septum on the tube. Low pressure conditions within the evacuated tube generate a flow of blood from the patient through the needle cannula and into the evacuated tube. The evacuated tube may be removed from the needle holder after a sufficient quantity of blood has been collected. One or more additional evacuated tubes may similarly be urged into the open end of the needle holder for drawing one or more additional samples of blood to be analyzed.

The needle cannula is withdrawn from the patient after a sufficient volume of blood has been collected for the required analytical procedures. The used needle cannula then must be shielded properly to avoid an accidental stick that could transmit a disease from the patient to the medical practitioner.

Many types of devices are available for shielding a used needle cannula. Some shields are hinged to the needle hub, and can be rotated from a first position, where the hinged shield is spaced from the needle cannula for use. After use, the hinged shield is rotated to a second position in shielding engagement around the needle cannula.

Other shields are telescoped over both the needle cannula and the needle hub. These shields initially are retained in a proximal position where the shield covers the hub but exposes the needle cannula for use. After use, the shield is telescoped distally to cover the needle cannula.

Most shielded needle assemblies are effective at performing their primary function of shielding a used needle cannula. However, many medical practitioners consider the available shieldable needle assemblies cumbersome. In particular, the shield that is telescoped over the needle hub typically will move relative to the needle cannula. Consequently, medical practitioners will grip the needle holder or other medical implement to which the shieldable needle assembly is mounted. However, a gripable region on the needle holder typically is relatively far from the distal end of the needle cannula and leads to at least a perception of poor control of the needle cannula. The perception of poor control increases as the length of the needle cannula is increased. As a result, needle assemblies with shields that telescope over the needle hub necessarily impose a limit on the length of the needle cannula that can be employed.

Additionally, in some cases, practitioners may be rushing and forget to operate the safety shield. Other situations arise where the patient moves suddenly or unexpectedly. Thus the needle cannula may inadvertently be pulled out of the vein and exposed with no time for the phlebotomist to initiate safety shielding. These weaknesses are not addressed adequately in prior art devices.

SUMMARY OF THE INVENTION

The present invention is directed to a needle assembly with means for shielding the user or patient end of the needle cannula. The needle assembly includes a needle cannula having opposed proximal and distal ends and a lumen extending between the ends. At least the distal end of the needle cannula may be pointed.

The needle assembly further includes a hub surrounding portions of the needle cannula. The hub includes opposed proximal and distal ends that are disposed between the proximal and distal ends of the needle cannula. The hub may be mounted securely to the needle cannula. Additionally, the proximal end of the hub may be provided with external structure for releasable engagement with a needle holder or with some other medical implement.

The needle assembly further includes a housing that may be attached to the hub. The primary function of the housing is to provide guidance for a shield telescoped between the needle cannula and hub. The housing partially encloses the shield and constrains shield motion in a longitudinal direction, substantially co-axial with the needle cannula. Additionally, the housing further includes external surface configurations to assist the user in manipulating the device during venous punctures. The housing may have external structure for releasable engagement with a needle holder or with some other medical implement.

The above-referenced shield of the needle assembly surrounds the needle cannula and is telescoped into the housing.

The shield initially is retained in a proximal position such that distal portions of the needle cannula are exposed for use. The shield can be moved from the proximal position to a distal position where the shield surrounds at least the pointed distal end of the needle cannula. The shield preferably is dimensioned to cover all of the needle cannula between the housing and the distal end of the needle cannula. Additionally, the shield preferably is constructed for locking engagement with the housing when the shield is in its distal position. Thus, the needle cannula cannot be re-exposed after shielding.

The needle assembly may further include biasing means for urging the shield from the proximal position to the distal position. The biasing means may comprise a coil spring disposed within the housing and extending between a portion of the hub and a portion of the shield. The spring may be in a compressed condition when the shield is in its proximal position. The spring then is operative to propel the shield to the distal position.

Actuating means are provided for releasing the shield from the proximal position and enabling the biasing means to propel the shield to the distal position. The actuating means may be actuated automatically and passively in response to an operational condition indicative of use of the needle assembly. For example, the needle assembly intended for use with an evacuated tube may have an actuating means that is triggered by the movement of the evacuated tube into communication with the proximal end of the needle cannula. Alternatively, the actuating means may comprise a latch that is accessible at an external location such as on the hub or housing.

The needle assembly of the present invention enables a medical practitioner to hold portions of the housing that surround the shield during venipuncture. Thus, the medical practitioner is able to grip a portion of the needle assembly relatively close to the distal end of the needle cannula. Gripping may be facilitated by structural elements disposed externally on the housing. Thus, for example, the housing may include at least one flat dimensioned and disposed for convenient gripping. Alternatively, the housing or hub may be provided with corrugations, dimples, recesses, concave surfaces, roughening or other structure that will facilitate manual gripping by a medical practitioner.

DESCRIPTION OF THE DRAWINGS

FIG. 5 is an exploded view of the cannula and hub sub-assembly as it fits within the housing and holder sub-assembly.

FIG. 6 is a partially exploded view of the cannula and hub sub-assembly aligned for assembly with the housing.

FIG. 7 is a magnified view of the portion of FIG. 6 showing the proximal end of the housing with snap retainers.

FIG. 8 is an exploded perspective view of a needle assembly with detached holder of the present invention.

FIG. 9 is an exploded perspective view of the needle assembly in FIG. 8 with non-patient shield detached.

FIG. 10 is an exploded perspective view of the needle assembly in FIG. 8 with the packaging and non-patient shields removed from the housing.

FIG. 11A is a front view of the housing of the present invention.

FIG. 11B is a sectional perspective view of the housing cut along the line depicted in FIG. 11A.

FIG. 11C is a sectional perspective view of the housing cut along the line depicted in FIG. 11A.

FIG. 12A is perspective view of the safety shield of the present invention.

FIG. 13 is an elevation view of the actuator of the present invention.

FIG. 14 is a perspective view of the actuator of the present invention.

FIG. 17 is an elevation view of the needle assembly during use before shielding.

FIG. 18 is an elevation view of the needle assembly after shielding.

FIG. 19A is a sectional view of the present invention shown before actuator safety shield release.

FIG. 19B is a sectional view of the present invention shown during actuator safety shield release.

FIG. 20A is a perspective sectional view of the present invention shown before actuator safety shield release.

FIG. 20B is a perspective sectional view of the present invention shown during actuator safety shield release.

FIG. 20C is a perspective sectional view of the present invention shown after actuator safety shield release but prior to complete shielding.

FIG. 20D is a perspective sectional view of the present invention shown after actuator safety shield release and after complete shielding.

DETAILED DESCRIPTION

Figure 1:
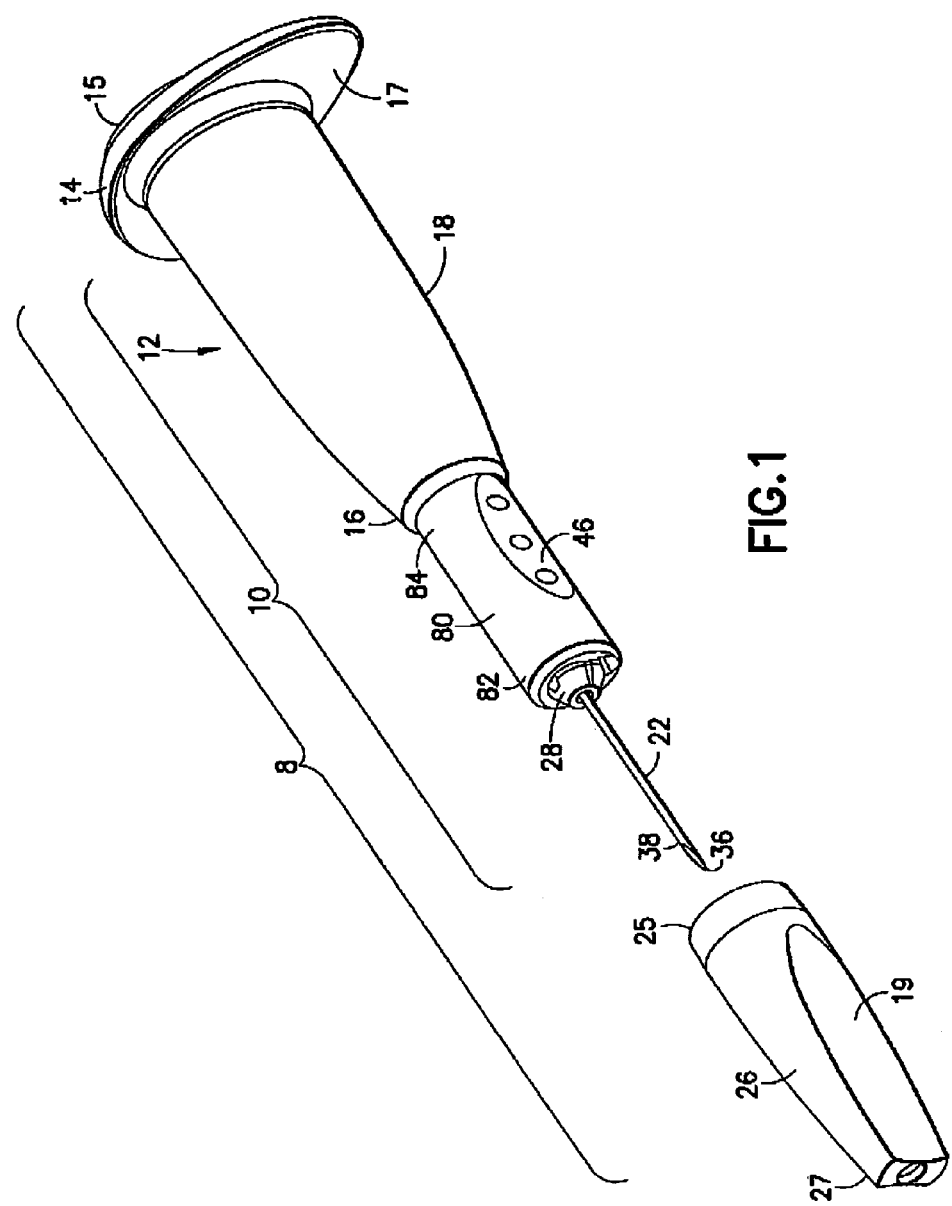
FIG. 1 is a perspective view of the needle assembly of the present invention.
Figure 2:
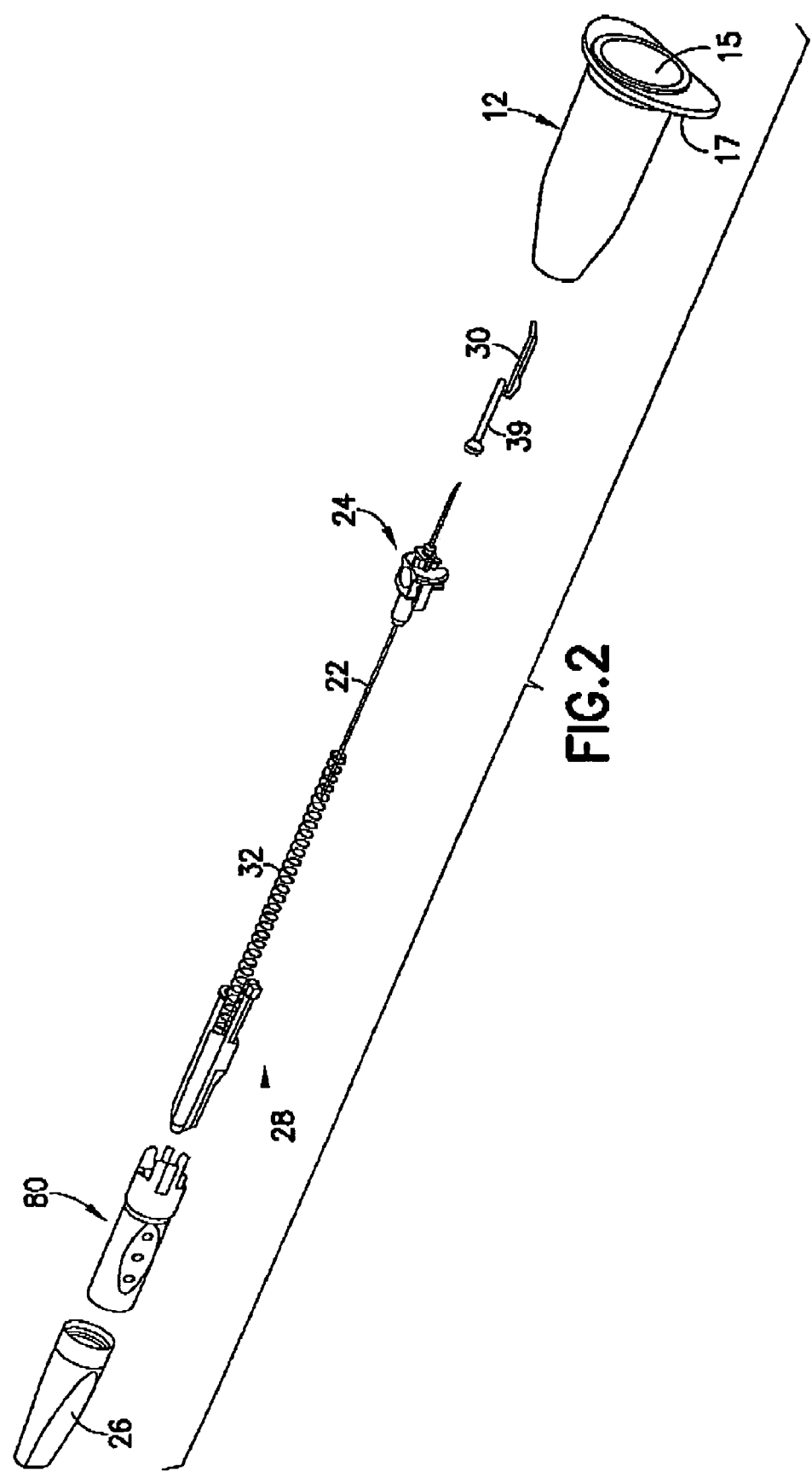
FIG. 2 is an exploded view of the device shown in FIG. 1.
Figure 3:
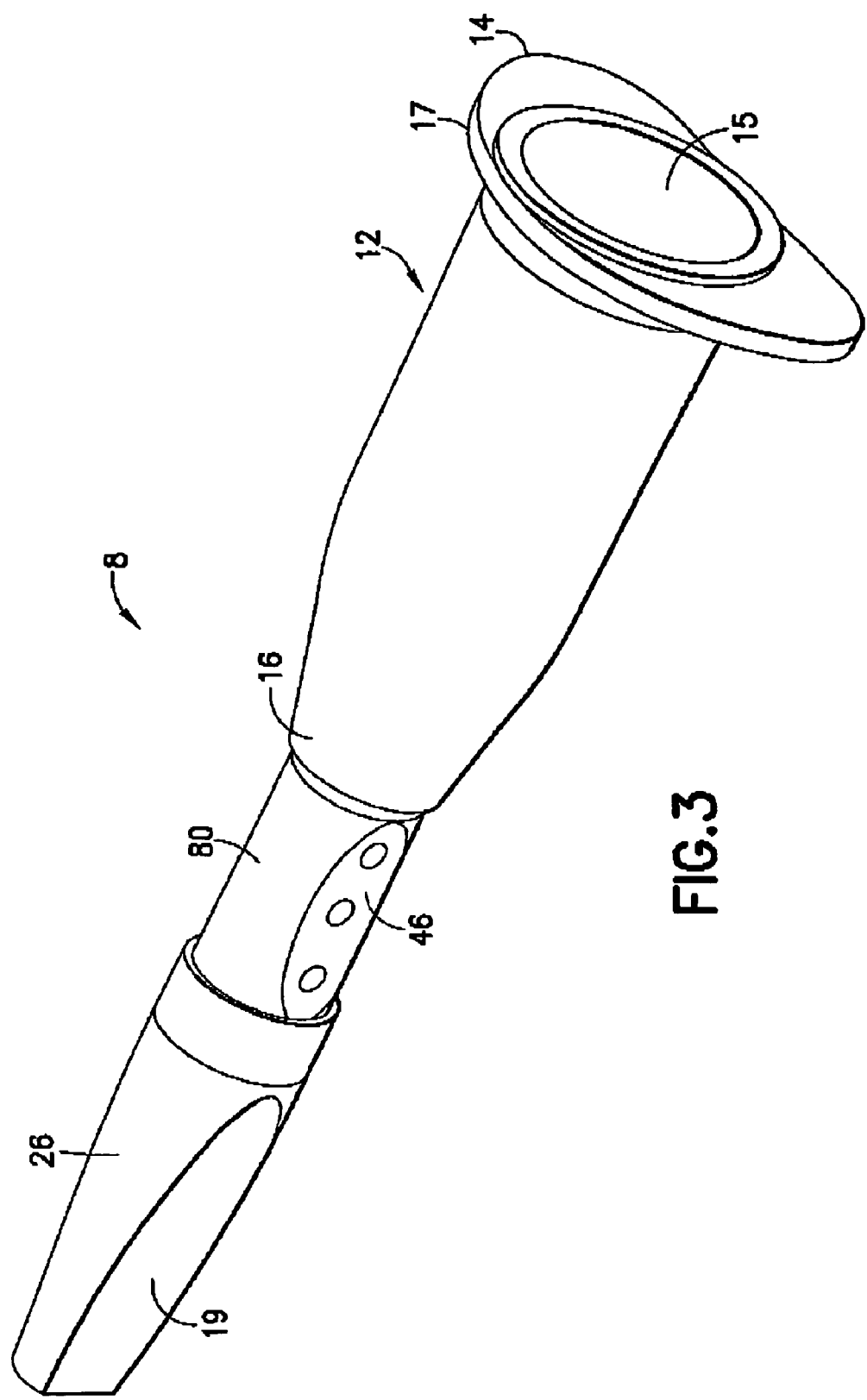
FIG. 3 is a perspective view with the packaging shield covering the needle cannula before use.
Figure 4:
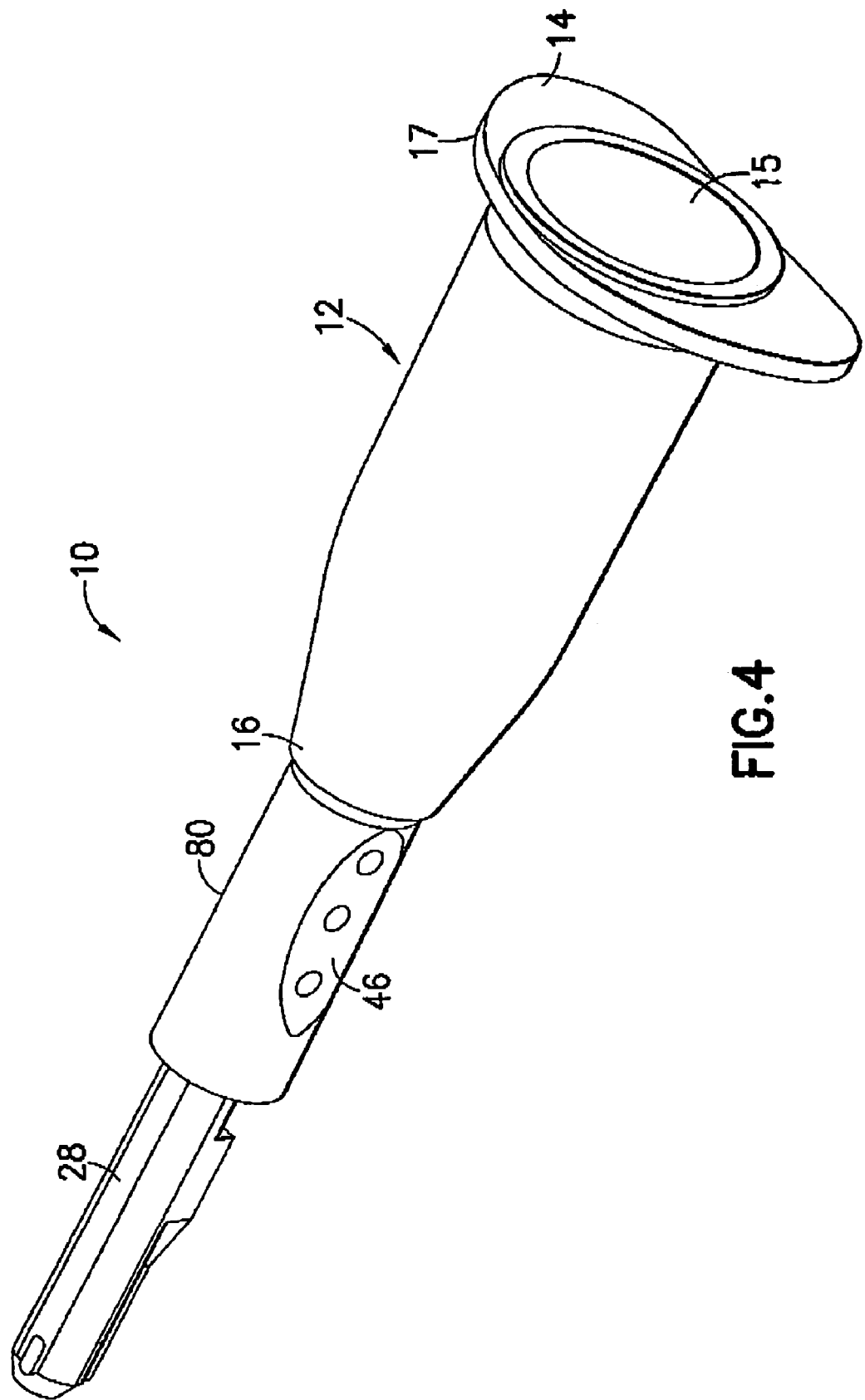
FIG. 4 is a perspective of FIG. 1 with the needle shield covering the needle cannula after use.

The needle assembly 10 of the present invention is shown in FIGS. 1–7 and 11–20. It will be noted that the term "distal" as used herein refers to the end of the needle assembly that punctures the patient's skin while "proximal" means the end of the needle assembly that punctures an evacuated container. Needle assembly 10 is mounted to a needle holder 12, as shown in FIGS. 1, 3, and 4. Needle holder 12 has a proximal end 14, a distal end 16 and a tubular sidewall 18 extending between ends 14 and 16. Proximal end 14 of needle holder 12 is widely open and is adapted to receive a blood collection tube 20 as shown in FIGS. 17, 19A–19D, and 20A–20D. However, proximal end 14 of holder 12 may have a removable seal or cap 15 for sterility. Proximal end 14 of holder 12 also has a radially aligned finger flange 17 to facilitate manipulation of holder 12. Flange 17 is non-circular to prevent holder 12 from rolling. Flange 17 preferably has a linear edge to provide a clear indication of the top and bottom sides. Distal end 16 of needle holder 12 includes structure to which needle assembly 10 is mounted. In particular, distal end 16 of needle holder 12 may be formed with non-threaded mounting means, such that needle holder 12 is substantially fixed to needle assembly 10 after assembly. The non-threaded mounting means comprises a combination of external rings 81 and keyways to secure needle assembly 10 axially and circumferentially. It is preferred that needle assembly 10 is mounted to needle holder 12 by the manufacturer so that the device is ready for fast and convenient use. Most importantly, pre-assembled needle assemblies 10 and needle holders 12 ensure that the proximal point of the needle is enclosed within holder 12 before, during, and after blood collection. Alternately, however, the distal end of the needle holder may be formed with an internal array of threads that are engagable by external threads on the needle assembly.

Needle assembly 10 ideally is packaged in a blister package having a thermoformed blister and top web. The top web is comprised of a material that may be permeable to gas such as ethylene oxide gas. Optionally, the proximal end 14 of holder 12 can be covered with a paper-like membrane that is thermally or adhesively sealed onto the proximal end 14 of the holder. Examples of materials used for a paper-like membrane are Tyvek® manufactured by DuPont and examples of materials to be used for a thermoformed blister package include glycol modified polyethylene terephthalate (PETG), polyethylene terephthalate (PET), high-density polyethylene, polypropylene, polycarbonate, nylon, and K-resin. In the configuration with a paper-like membrane covering the open proximal end 14 of holder 12, a thermoformed blister and top web would not be required, and the entire assembly can be sterilized by ethylene oxide gas or cobalt 60 irradiation.

Needle assembly 10 includes a needle cannula 22, a needle hub 24, a packaging shield 26, a safety shield 28, a sleeve 39, a housing 80, an actuator 30, and a spring 32. In other embodiments, a portion of the needle assembly (e.g., the housing) can be integral or unitary with the needle holder to reduce assembly steps by the manufacturer and the user.

Needle cannula 22 includes a pointed proximal end 34, as shown in FIGS. 1, 5 and 6, a sharply beveled distal end 36 and a lumen 38 extending therebetween. Proximal end 34 of needle cannula 22 is covered by an elastomeric multiple sample sleeve 39 (shown in FIGS. 2, 9 and 10) that can be pierced by pointed proximal end 34 of needle cannula 22.

Figure 15:
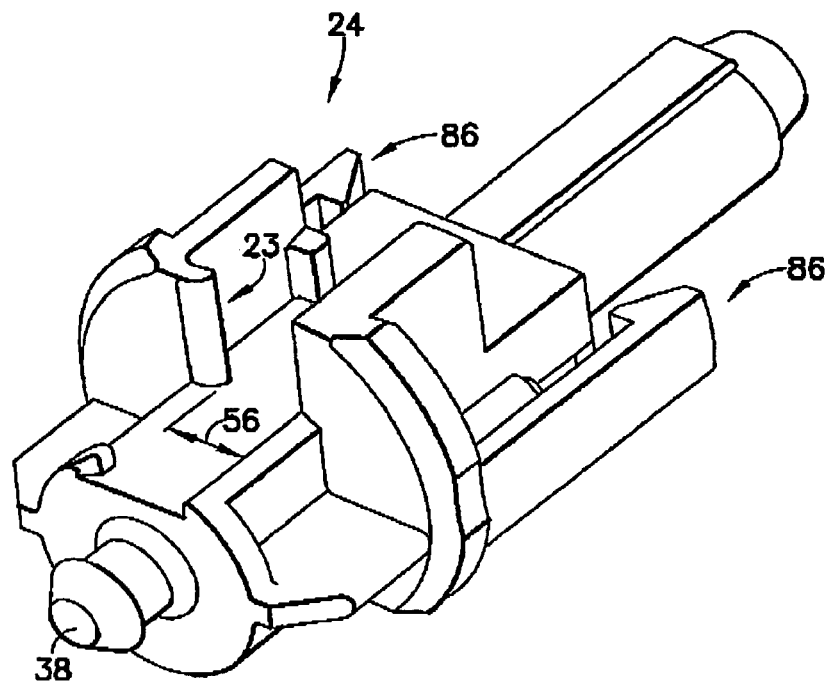
FIG. 15 is a perspective view of the hub of the present invention.
Figure 16:
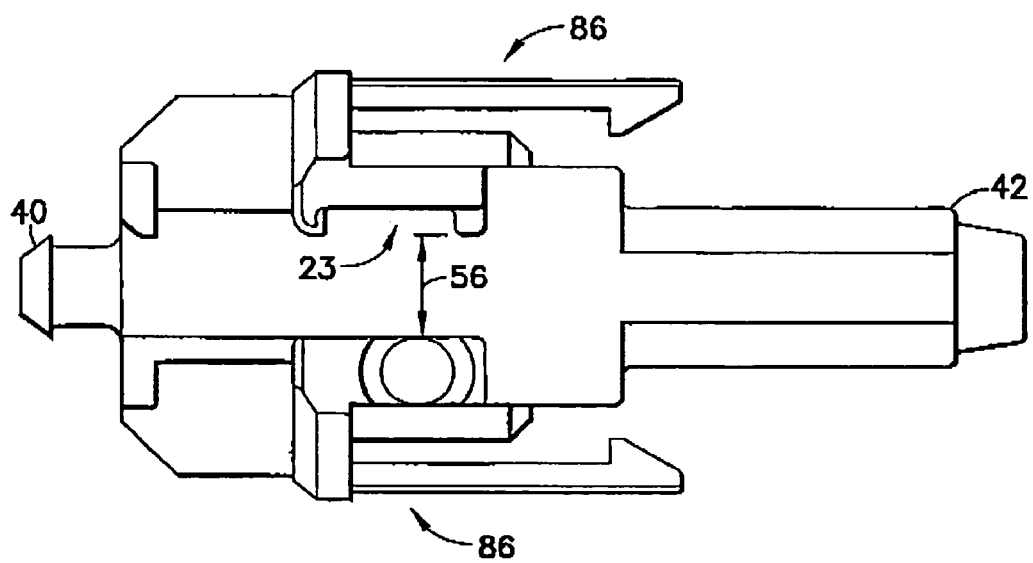
FIG. 16 is an elevation view of the hub of FIG. 15.

Needle hub 24 is illustrated in greater detail in FIGS. 15 and 16. Needle hub 24 includes a proximal end 40, a distal end 42, and a lumen 38 extending therebetween. Housing attachment means is provided externally of hub 24 to achieve fixed engagement between hub 24 and needle housing 80. The housing attachment means may include ultrasonic welding, heat staking, solvent bonding, mechanical latches with receiving latch detents, adhesive bonding, friction fit joints, irreversible threads, or any of the like. In the embodiment of FIGS. 5, 6, 7, 15 and 16 the housing attachment means are defined by mechanical latches 86 that extend distally from needle hub 24 for engagement in detents 88 on needle housing 80. Hub 24 is mounted securely to locations on needle cannula 22 between proximal and distal ends 34 and 36 thereof and in a specified rotational orientation relative to the bevel at distal end 36 of needle cannula 22. More particularly an adhesive well is formed on needle hub 24 and receives adhesive to bond needle cannula 22 to hub 24. Alternately, needle hub 24 and needle housing 80 may be combined as one molded component. However it is generally easier to manufacture needle hub 24 and housing 80 as two components.

Needle housing 80 is illustrated in greater detail in FIGS. 11A–11C. Needle housing 80 includes a proximal end 82, a distal end 84 and a tubular wall 44 extending between ends 82 and 84. As shown in FIGS. 11A–11C, tubular wall 44 is of generally circular or elliptical cross-section. Alternately, tubular wall 44 may have a non-circular cross-section or rectangular cross-section. The specific cross-sectional shape is not critical, and shapes other than those shown herein are contemplated. Housing 80 preferably is formed from a transparent or translucent material to permit user observation of safety shield 28. Thus, the medical practitioner can observe movement of safety shield 28, as explained below, to provide a visual indication that proper shielding is taking place. Additionally, proximal end 82 of housing 80 may have one of many optional means for attachment to a needle holder 12, such as a threaded connection, interference fit, adhesive bonding, solvent bonding, ultrasonic welding, heat staking, snap fit, or any other means. More specifically, the housing may have external threads and may be mounted to internal threads of the distal end of the needle holder. Alternately, housing 80 has non-threaded mounting means to engage holder 12 in an interlocking manner. External rings 81 are illustrated in FIGS. 5–7 and define one preferred non-threaded mounting means that provide sufficient frictional or interlocking forces to resist housing 80 from unintentionally releasing from holder 12 during puncturing of septum 21 by proximal end 34 of needle cannula 22. In the illustrated embodiment, hub 24 is mounted indirectly to the holder 12 through needle housing 80. Housing 80 preferably is non-rotatably mounted to holder 12 to ensure that the bevel at distal end of needle cannula 22 faces up relative to the bottom edge of flange 17 of holder 12. Distal end 84 of needle housing 80 is characterized by diametrically opposed V-shaped notches as shown in FIG. 11B. Notches 85 cooperate with corresponding structure on packaging shield 26.

Housing 80 has a length such that distal end 84 of housing 80 is spaced proximally from distal end 36 of needle cannula 22 sufficiently to enable convenient use of needle cannula 22. Portions of tubular wall 44 from distal end 84 toward proximal end 82 of housing 80 are spaced outwardly from needle cannula 22 for permitting telescoped movement of safety shield 28 between needle cannula 22 and housing 80, as explained further below. Additionally, as shown in FIGS. 1, 3, and 4, tubular sidewall 44 of housing 80 is provided with external surface configurations or grips 46 to facilitate digital manipulation. Surface configurations or grips 46 include elongate recesses or flats having small bumps thereon. However, other surface configurations may be employed, such as a plurality of ridges or grooves, or concave detents shaped to conform to a user's fingers. Grips 46 preferably are orthogonal to the bottom edge of finger flange 17 of holder 12.

Housing 80 has internal features to restrict movement of safety shield 28 relative to housing 80. Tubular wall 44 of housing 80 is formed with a first proximal facing stop surface 48. As shown in FIG. 11B, housing 80 further includes an axially extending latch channel 52 formed on an upper interior surface of tubular wall 44. Latch channel 52 extends from the first proximal facing stop surface 48 shown in FIG. 11C to a location substantially adjacent distal end 84 of housing 80 as shown in FIG. 11B. A distal detent 47 is located near the distal end of tubular wall 44 of housing 80, as shown, and is at the distal end of latch channel 52. Distal detent 47 has a distally facing stop surface 54. Distal detent 47 and distally facing stop surface 54 are dimensioned to receive a latch 68 on safety shield 28, as explained below. Tubular wall 44 further includes a stop channel 50 extending distally and ending with a second proximally facing stop surface 58 near distal end 82 of housing 80 as shown in FIG. 11C.

Distal end 36 of needle cannula 22 is used to pierce the patient's skin and must be kept very sharp. Thus a packaging shield 26, as shown in FIGS. 1–3 and 8–10, is used to enclose the distal end 36 of needle cannula 22. The packaging shield 26 preferably is formed with two opposing relatively flat walls 19 to facilitate easy handling by the phlebotomist who is likely to be wearing gloves that may even be wet with alcohol prep solution. In the embodiment shown, the open end of the packaging shield 26 fits partially over the distal end 84 of housing 80. The packaging shield 26 and housing 80 are dimensioned so that there is an interference fit that desirably provides a sterile barrier between the packaging shield 26 and housing 80 in those embodiments that do not employ blister packaging. In those embodiments, the interference fit between packaging shield 26 and housing 80 they make separation of packaging shield 26 difficult. Accordingly, for those embodiments, packaging shield 26 is provided with a pair of diametrically opposed ribs (not shown) on the interior surface. The ribs terminate at a V-shaped point or an arcuate end facing toward the open end of packaging shield 26. The ends of the ribs are disposed, dimensioned and configured to mate with the V-shaped notches 85 at distal end 84 of housing 80. The engagement of the ends of the rib with V-shaped notches 85 develops ramping forces in response to twisting of packaging shield 26. Thus, the rotational movement applied to packaging shield 26 generates a corresponding axial movement of packaging shield 26 relative to housing 80, and hence facilitates separation of packing shield 26. Additionally, a tamper-evidence indicator may be placed between the packaging shield 26 and the housing 80 to provide indication of prior usage.

Safety shield 28, as shown in FIGS. 12A–12D, includes a proximal end 60, a distal end 62 and a substantially tubular sidewall 64 extending between the ends. Tubular sidewall 64 of safety shield 28 preferably is imprinted with indicia at a location aligned with the bevel-up side of needle cannula 22. This is the portion of tubular sidewall 64 that will be the most visible to the medical practitioner. The existence of indicia on this portion of tubular sidewall provides a physical indication to the medical practitioner that shielding is taking place. The indicia should be in a form that will provide evidence of movement. For example, a plurality of intermittent markings or a marking that changes its dimensions along its length would be most beneficial. Safety shield 28 initially is retained releasably in a proximal position with at least a major portion of safety shield 28 disposed in the space between needle cannula 22 and tubular wall 44 of housing 80. In this proximal position, proximal end 60 of safety shield 28 is substantially adjacent first proximally facing stop surface 48 of housing 80. Additionally, as shown in FIG. 1, distal end 62 of safety shield 28 is flush with or projects only slightly from distal end 84 of housing 80 when safety shield 28 is in its proximal position. Safety shield 28 can be released from its proximal position and is movable to a distal position that is shown in FIGS. 4, 18, 19D and 20D. When moved into its distal position, safety shield 28 completely covers portions of needle cannula 22 between needle hub 24 and distal end 36 of needle cannula 22.

Figure 12B:
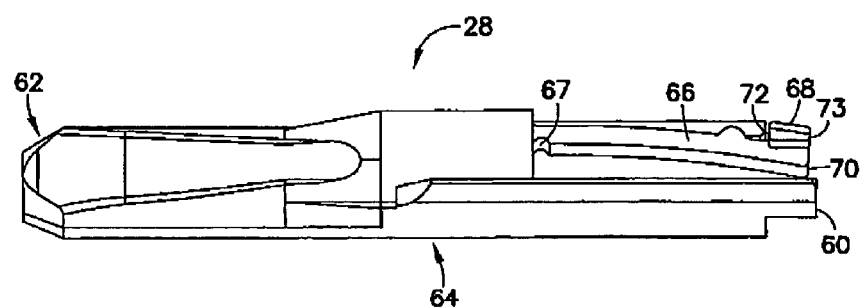
FIG. 12B is a perspective view of the needle shield of the present invention.
Figure 12C:
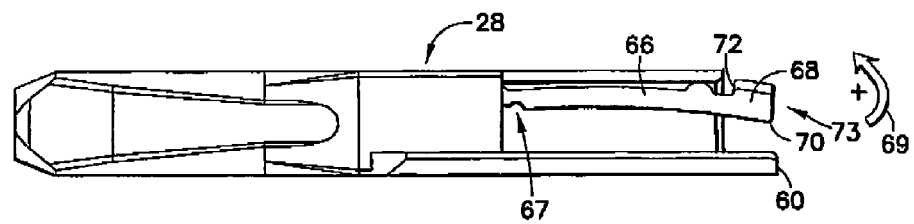
FIG. 12C is an elevation view of the needle shield of the present invention with the deflectable member in an unbiased position.
Figure 12D:
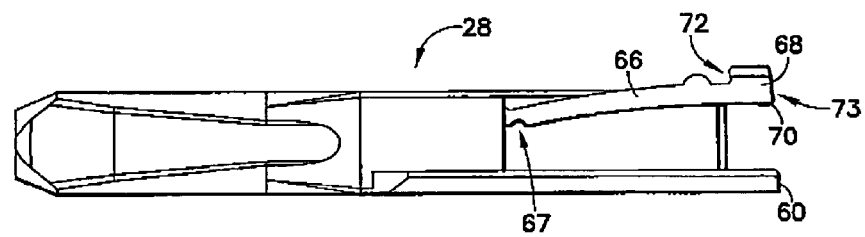
FIG. 12D is an elevation view of the needle shield of the present invention similar to FIG. 12C, but with the deflectable member in a deflected state.

As shown in FIGS. 12B–12D, safety shield 28 has a hinged deflectable member 66 that is cantilevered toward proximal end 60. Deflectable member 66 is deflectable outwardly or in a transverse direction. A latch 68 is formed on deflectable member 66 near proximal end 60 of safety shield 28 and enters latch channel 52 when deflectable member 66 is deflected outwardly. Hinged deflectable member 66 further includes a cam surface 70 at the extreme proximal end thereof. Cam surface 70 is aligned at an acute angle to a radial plane passing through needle assembly 10. Axially aligned distally directed forces on cam surface 70 will generate a transverse deflection of deflectable member 66 so that latch 68 enters into latch channel 52. Latch 68 further includes a distal facing locking face 72, and a proximally facing locking face 73. Both locking faces 72 and 73 are aligned substantially perpendicular to the axis of needle assembly 10. FIG. 12C shows deflectable member 66 in its non-deflected state and FIG. 12D shows deflectable member 66 in its deflected state. Distal movement of actuator 30 moves deflectable member 66 from the position shown in FIG. 12C in direction 69 depicted in FIG. 12C to the position shown in FIG. 12D until latch 68 is no longer resisted by first proximally facing stop surface 48 of housing 80 and therefore is free to move distally with respect to the needle cannula 22 under spring energy supplied by spring 32.

Safety shield 28 further includes a stop 74 disposed substantially diametrically opposite latch 68. Stop 74 is in a plane passing through the axis of needle assembly 10 and includes a locking surface 76 facing in the distal direction as shown in FIG. 12A. Stop 74 prevents spring 32 from pushing safety shield 28 past housing 80.

Hub 24 is connected to the proximal end 82 of housing 89. Hub 24 further includes an actuator channel 56 extending substantially parallel to housing 80 as shown in FIGS. 15 and 16. Actuator 30, as shown in FIGS. 13 and 14, is disposed slidably in actuator channel 56 of hub 24. Actuator 30 includes a proximal end 78 substantially adjacent to needle cannula 22 that will lie within needle holder 12. Actuator 30 also includes a distal end 79 that will lie substantially adjacent cain surface 70 of latch 68. Distal end 79 of release actuator 30 is angularly aligned to mate with cam surface 70 of latch 68, such that distal movement of release actuator 30 will generate transverse deflection of deflectable member 66.

As shown in FIGS. 13 and 14, actuator 30 has an integrated anti-reset feature or latch 29 that interfaces with hub 24 upon activation of the device. Once a tube 20 is inserted and interfaces with the proximal end 78 of actuator 30, latch 29 will interface with the hub channel 56 thus deforming latch 29 temporarily inward thereby permitting latch 29 to advance into latch recess 23. Once latch 29 is within latch recess 23, latch 29 will return resiliently towards an undeflected position so that actuator 30 is prevented from moving back to a proximal position that would allow safety shield 28 to be completely reset to its original position.

A spring 32 surrounds portions of needle cannula 22 that are surrounded by safety shield 28. Thus spring 32 is compressed to retain stored energy when safety shield 28 is in the proximal position within tubular wall 44 of housing 80. Spring 32 then will propel safety shield 28 distally after activation. The proximal end 31 of spring 32 remains in fixed relation to the holder 12, hub 24, and housing 80 while the distal end 33 of spring 32 moves relative to the holder 12, hub 24, and housing 80.

The force applied by spring 32 to safety shield 28 is essential to proper operation of needle assembly 10. In particular, spring 32 must exert sufficient force to ensure that safety shield 28 will be propelled sufficiently toward distal end 36 of needle cannula 22 to complete its essential shielding function. However spring 32 should not exert enough force to push needle cannula 22 out of the patient. Additionally, forces exerted by safety shields 28 on the skin of the patient should not be so large as to cause a patient to react and move suddenly away from the shield. A spring force of 0.02–0.20 pounds, and preferably about 0.09 pounds has been found to meet the objectives of ensuring complete shielding without excessive force against the skin of the patient. Additionally, a fine lubricating spray may be applied to the sliding parts of safety shield 22, hub 24 and/or housing 80 to ensure complete and efficient movement of safety shield 28 with a low spring force.

Needle assembly 10 is used by attaching proximal end of hub 24 and housing 80 into needle holder 12 such that proximal end 34 of needle cannula 22 and proximal end 78 of actuator 30 lie within needle holder 12. Packaging shield 26 then is removed from housing 80 to expose pointed distal end 36 of needle cannula 22. The medical practitioner then manually engages housing 80 at grips 46 and guides distal end 36 of needle cannula 22 into a targeted vein of a patient Activation of shield 28 is achieved automatically and passively by insertion of blood collection tube 20 into proximal end 14 of needle holder 12. Sufficient insertion of blood collection tube 12 will cause proximal end 34 of needle cannula 22 to pierce through the elastomeric septum 21 that extends across the open end of blood collection tube 20, as shown in FIGS. 19A–19D. Distal movement of blood collection tube 20 into needle holder 12 also will cause blood collection tube 20 to engage proximal end 78 of actuator 30, thereby causing actuator 30 to slide distally through actuator channel 56 of hub 24 This distal movement of actuator 30 will cause distal end 79 of actuator 30 to engage cam surface 70 of hinged deflectable member 66 of safety shield 28 with sufficient force to pivot deflectable member 66 transversely about binge 67 sufficiently to disengage locking face 72 of latch 68 from first proximally facing stop surface 48 of housing 80.

Figure 19C:
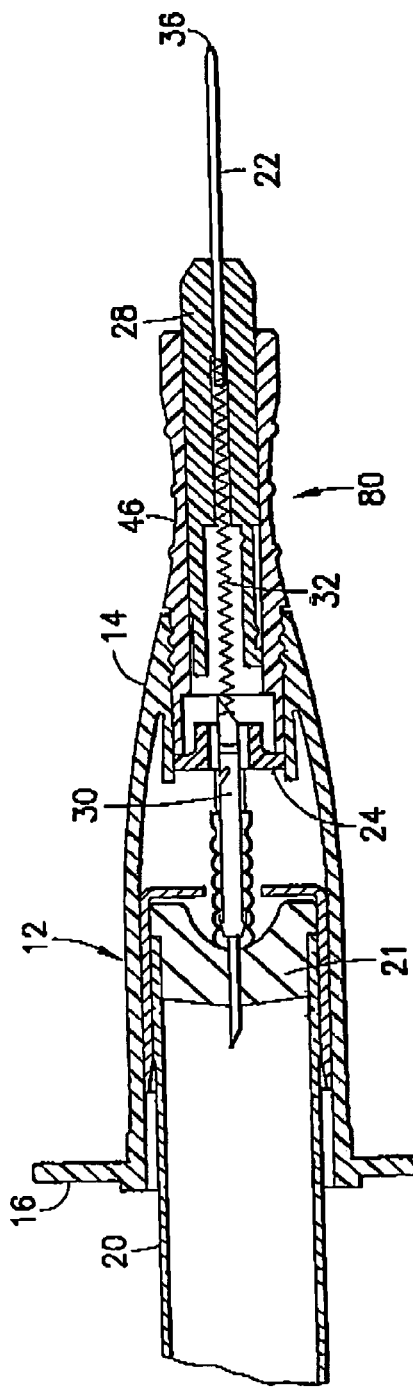
FIG. 19C is a sectional view of the present invention shown after actuator safety shield release but prior to complete shielding.
Figure 19D:
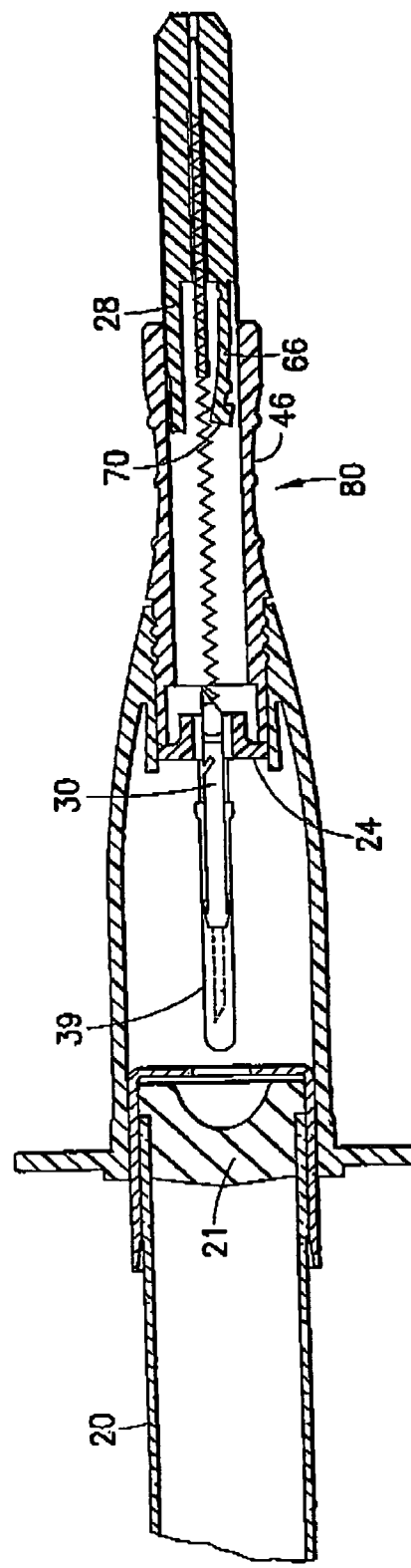
FIG. 19D is a sectional view of the present invention shown after actuator safety shield release and after complete shielding.
Figure 21:
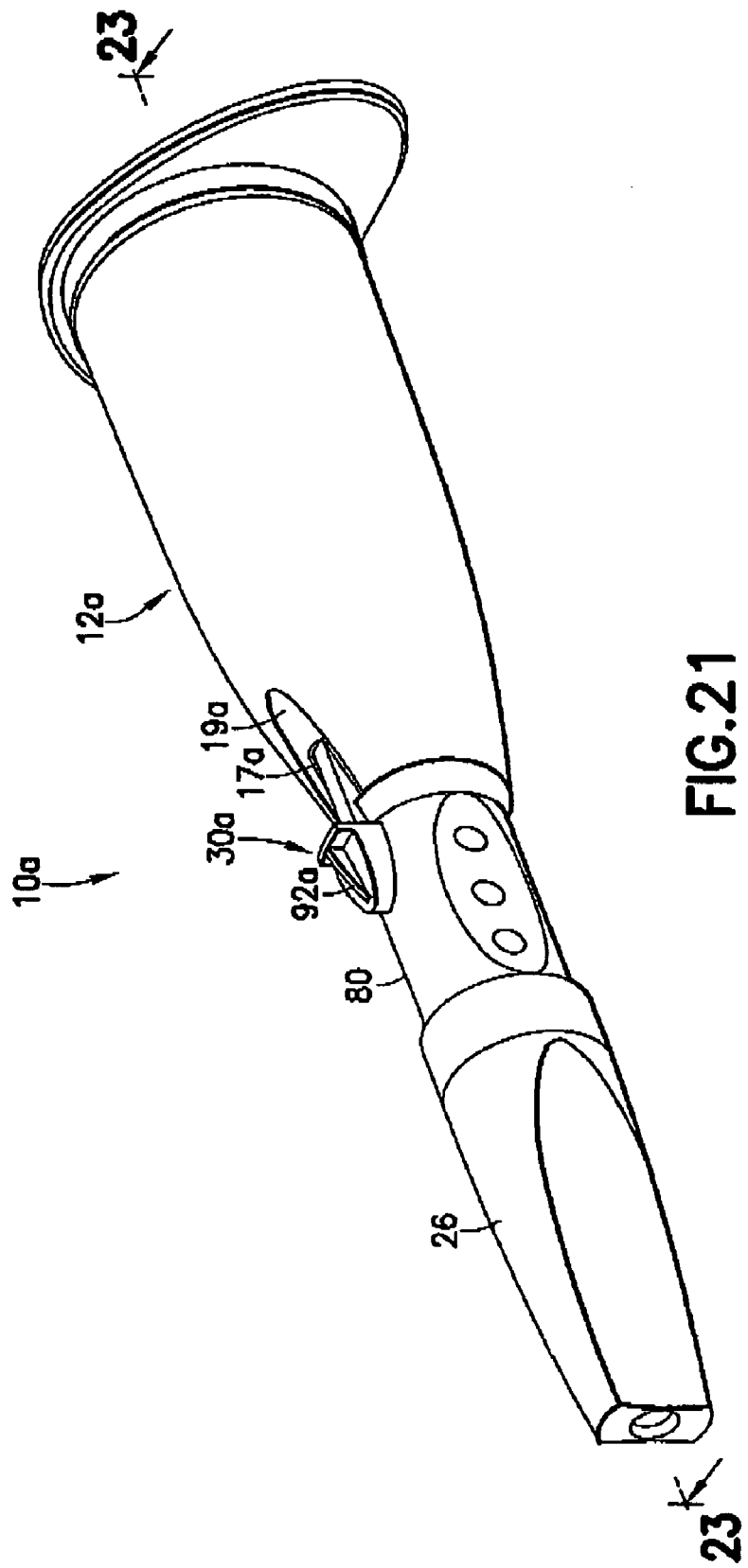
FIG. 21 is a perspective view of an alternate needle assembly of the present invention prior to use and with the packaging shield covering the needle cannula.
Figure 22:
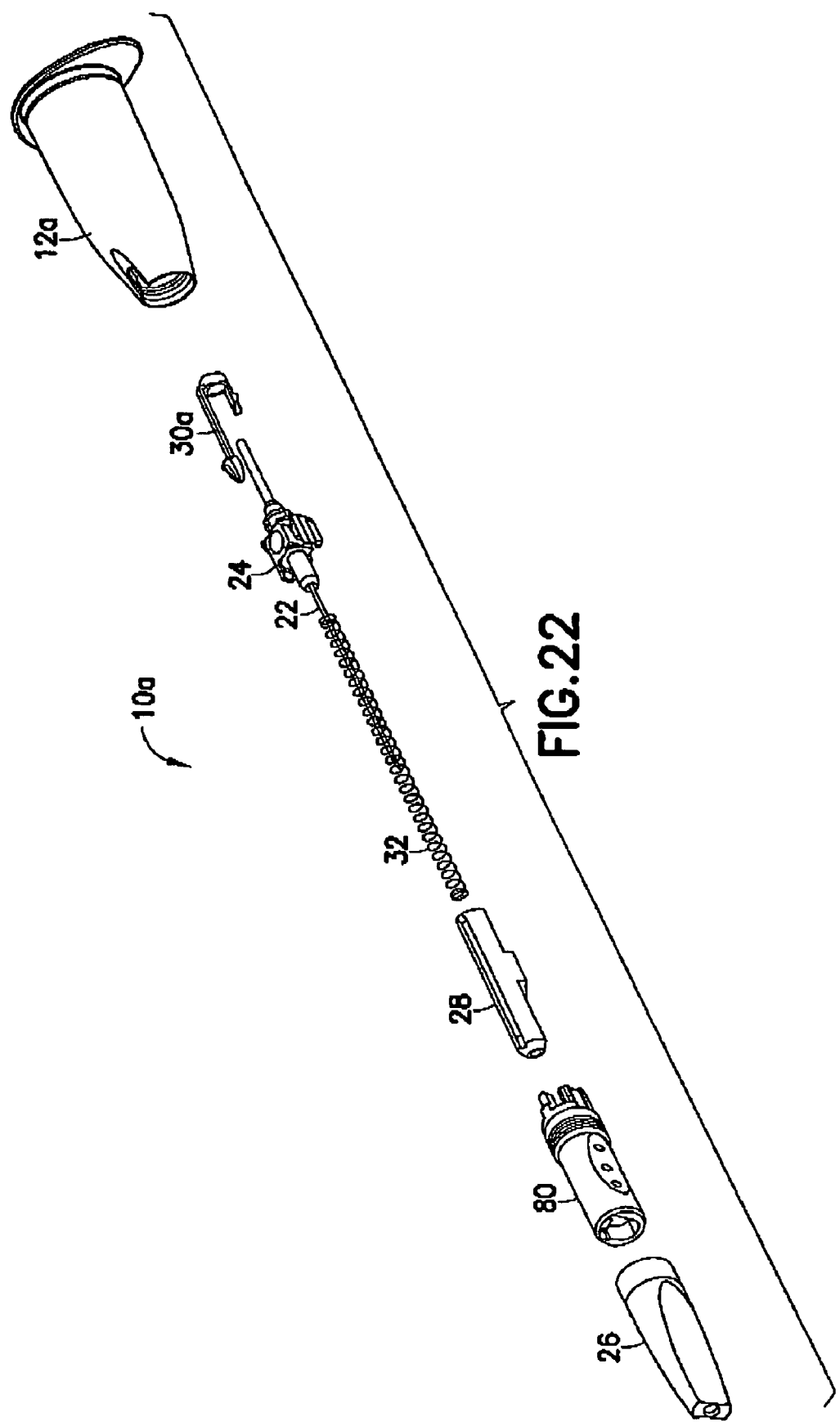
FIG. 22 is an exploded perspective view similar to FIG. 2, but showing the alternate embodiment of FIG. 21.
Figure 23:
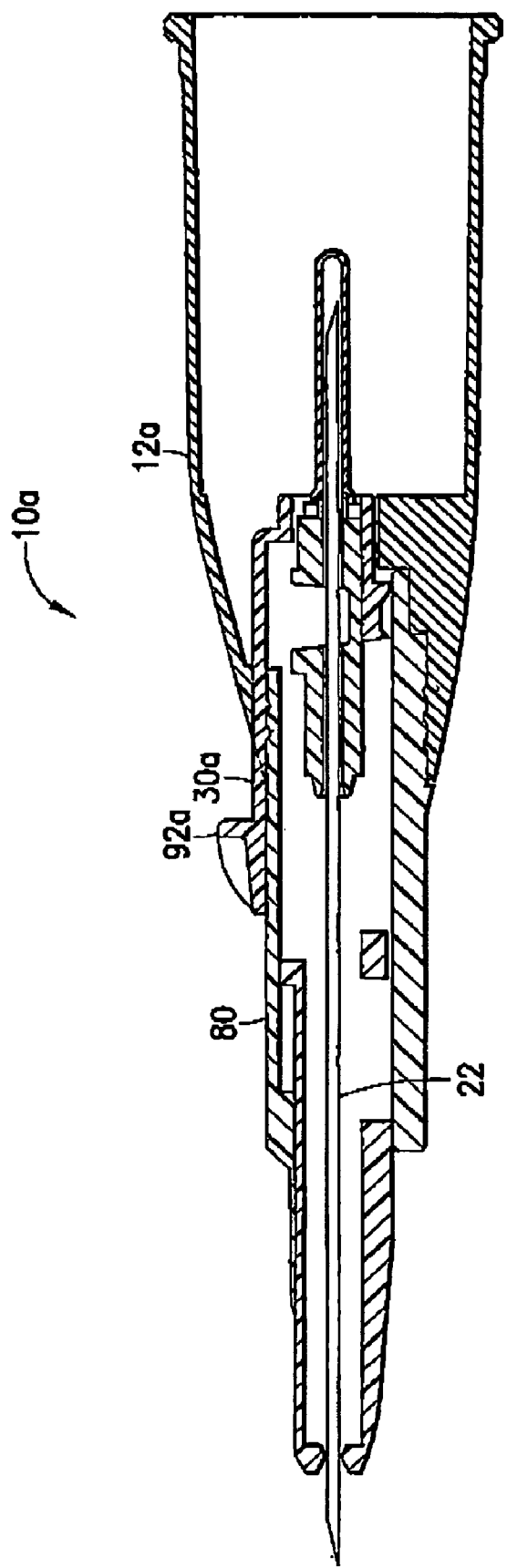
FIG. 23 is a cross-sectional view taken along line 23—23 in FIG. 21.

Disengagement of latch 68 from first proximally facing stop surface 48 into latch channel 52 causes safety shield 28 to be propelled distally under the action of spring 32. Latch 68 will be guided in latch channel 52 as safety shield 28 is moved toward distal end 84 of housing 80. Sufficient distal movement of safety shield 28 will cause latch 68 to engage in distal detent 47 of housing 80. While in distal detent 47, latch 68 interferes with distal facing stop surface 54 and prevents safety shield 28 from being unshielded. Additionally, stop 74 on safety shield 28 rides along stop channel 50 until stop 74 engages second proximally facing stop surface 58 thereby preventing safety shield 28 movement in the distal direction after needle point 36 has been shielded. As a result of stop 74 and latch 68, safety shield 28 is prevented from moving either distally or proximally from this locked position as shown in FIGS. 18, 19D, and 20D.

Figure 24:
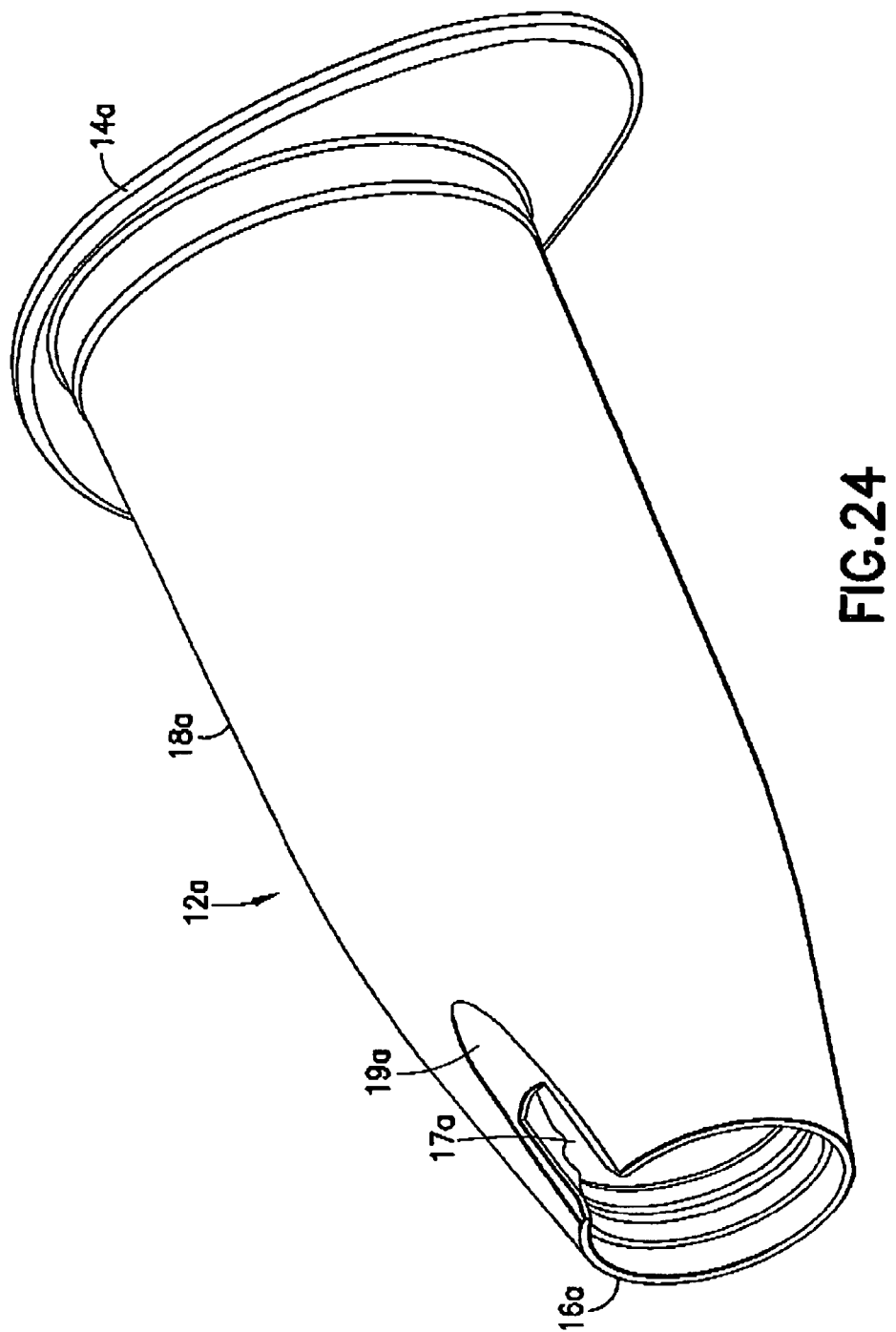
FIG. 24 is a perspective view of the holder for use with the embodiment of FIGS. 21–23.
Figure 25:
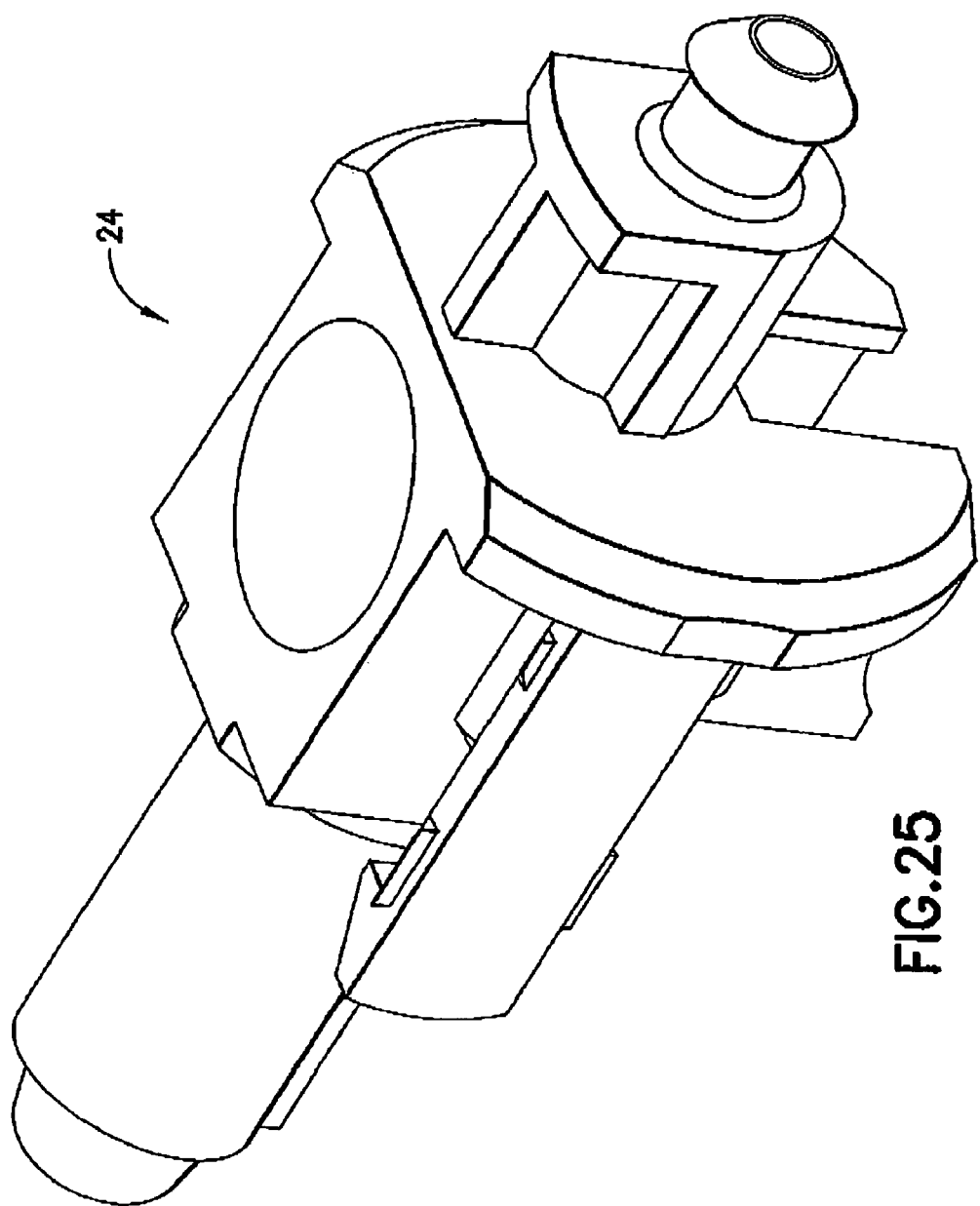
FIG. 25 is a perspective view of the hub for use with the embodiment of FIGS. 21–24.

The above-described needle assembly is completely passive in that shielding is achieved without any required user activation other than the normal insertion of a fluid collection tube into the open proximal end 14 of holder 12. There may be instances, however, where a user may want direct control over the initiation of shielding or where a user may want dual control where shielding can be actuated by insertion of a fluid collection tube and/or by direct digital activation by the user. These options can be achieved without a complete redesign of the above-described needle assembly. In particular, an alternate needle assembly is identified generally by the numeral 10a in FIGS. 21–27. Assembly 10a include a needle cannula 22, a hub 24, a packing shield 26 and a housing 80, all of which are substantially identical to corresponding parts of the first embodiment described and illustrated above. However, assembly 10a includes a holder 12a that is slightly different from holder 12 described and illustrated above. In particular, as shown most clearly in FIG. 24, holder 12a includes a tubular sidewall 18a that has a proximal end 14a, a distal end 16a. A notch 17a extends into tubular sidewall 18a at distal end 16a. Additionally, notch 17a is disposed on a portion of sidewall 18a that will align with the bevel-up side of needle cannula 22. Notch 17a is partly surrounded by an elongate flat or recess 19a in tubular sidewall 18a to minimize the projection of an actuator, as explained herein and to provide a visible indication of a region to be accessed by a user for carrying out a manual actuation of the shielding.

Figure 26:
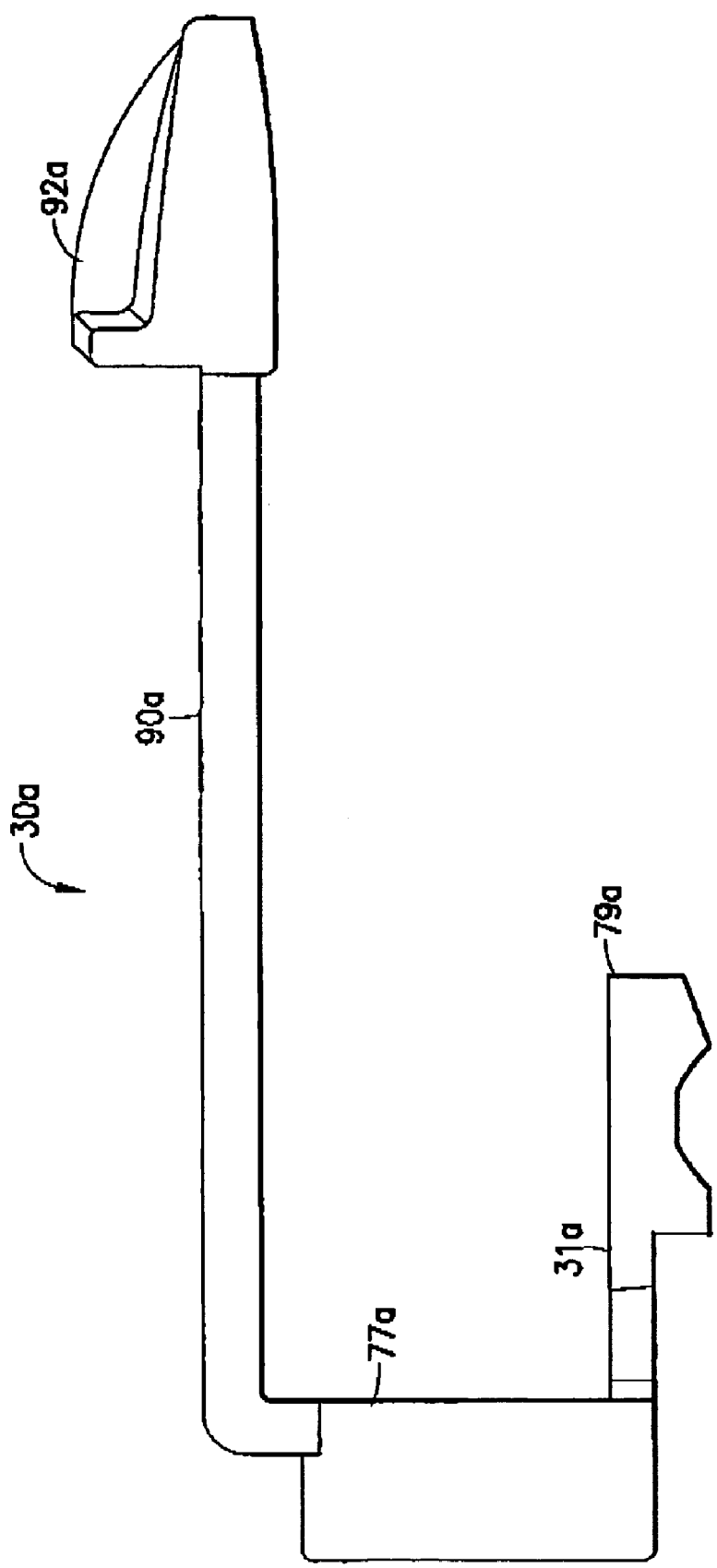
FIG. 26 is a side elevational view of the actuator of the embodiment of FIGS. 21–25.
Figure 27:
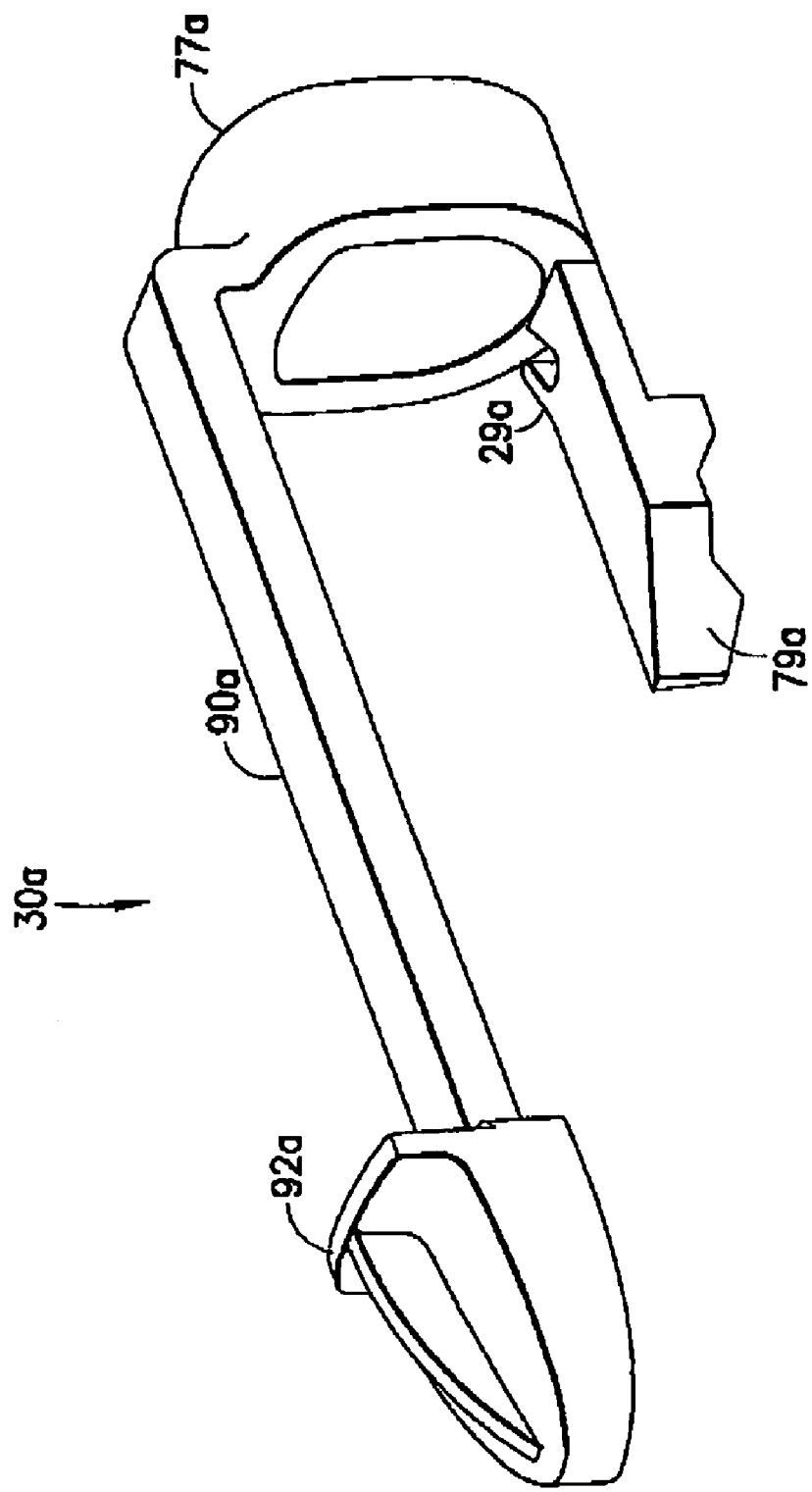
FIG. 27 is a perspective view of the actuator of FIG. 26.

Needle assembly 10a further includes an actuator 30a as shown in FIGS. 26 and 27, that differs from actuator 30 described above and illustrated in FIGS. 13 and 14. In particular, actuator 30a includes an actuating beam 31a with a distal end 79a that is structurally and functionally virtually identical to distal end 79 of actuator 30. Additionally, actuating beam 3k includes an anti-reset latch 29a that is structurally and functionally substantially identical to latch 29 of actuator 30. Actuator 30a further includes a mounting collar 77a that is disposed and configured to mount slidably over proximal portions of hub 24. Additionally, mounting collar 77a is dimensioned for slidable disposition within holder 12a. Actuator 30a further includes an arm 90a that projects distally from collar 77a. Ann 90a is dimensioned for slidable insertion in notch 17a of holder 12a, and terminates at an actuating button 92a.

Needle assembly 10a is assembled substantially as needle assembly 10, described and illustrated above. However, collar 77a of actuator 30a is slidably disposed over and around proximal portions of hub 24. The subassembly of needle cannula 22, hub 24, packing shield 26, housing 80 and actuator 30a can be mounted in bolder 12a substantially as described above. However, arm 90a will project slidably through notch 17a such that actuating button 92a is slidably disposed on the outer circumferential surface of housing 80.

Needle assembly 10a is used substantially in the conventional manner as explained above. However, safety shield 28 is actuated by digital pressure exerted by a thumb or forefinger of the user on actuator button 92a. In particular, the user urges actuator button distally along outer surface of housing 80 a sufficient distance for distal end 79a of actuator 30a to actuate safety shield 28 as explained above.

Figure 28:
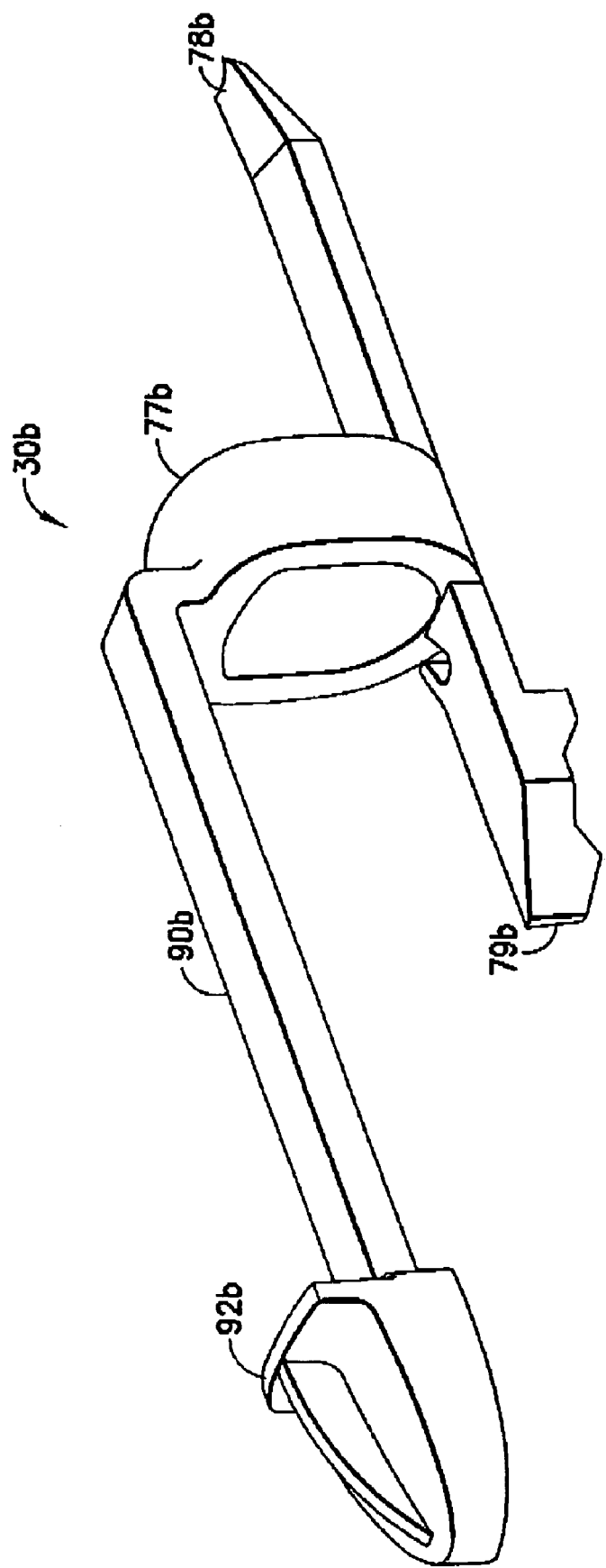
FIG. 28 is a perspective view of an alternate embodiment of the actuator that permits both manual actuation and tube actuation of the shield.

In certain instances, a user may want to have the ability to shield the needle cannula independently of the passive actuation described above with respect to the first embodiment. For example, a user may have some reason to terminate a specimen collection procedure prior to insertion of an evacuated tube into the holder. This objective can be achieved by alternate actuator 30b. Actuator 30b is effectively a hybrid of actuator 30 and actuator 30a. Specifically, actuator 30b, as shown in FIG. 28, is identical to actuator 30a in all respects, but further includes a proximal end 78b that is identical to proximal end 78 of actuator 30. Thus, actuator 30b permits shielding to be completed either by insertion of an evacuated tube into holder or by digital pressure on actuator button 92b.

The internal disposition of safety shield 28 within the housing in any of these embodiments provides several significant advantages. In particular, a medical practitioner employing needle assembly 10 can hold needle assembly 10 much closer to distal end 32 of needle cannula 22. This distal location for gripping needle assembly 10 provides better balance and feel for the medical practitioner and facilitates alignment and aiming of needle assembly 10.

Alternately to the embodiments described above, the needle assembly can be made in a detachable holder or hard pack assembly 100 configuration using all the components of the needle assembly described above with the addition of a non-patient needle shield 90 for enclosing proximal end 34 of needle cannula 22 shown in FIGS. 8–10. Non-patient needle shield 90 is reversibly detachable to one or both of needle housing 80 and hub 24. The user removes non-patient needle shield 90 from hardpack assembly 100 and attaches holder 12 to the proximal end of housing 80 prior to use. Once holder 12 is attached to housing 80, the user can remove packaging shield 26 and use the needle device in a similar manner to the needle assembly embodiment described herein.

It will be apparent that other variations can be made to the present invention without departing from the scope of the invention as defined by the appended claims. In alternate embodiments, the actuator can deflect a latch radial inwardly or in some other direction to effect disengagement from the housing. In addition, the actuator and the latch may be configured to generate rotation of the shield relative to the housing for disengaging a latch on the shield from a detent on the housing. Still further, other configurations for the exterior of the housing may be provided for convenient and secure digital manipulation, such as the exterior of the shield may include an array of ribs, grooves or dimples instead of or in addition to the flats shown in the illustrated embodiments.

In a further embodiment, the invention provides a method of making a blood collection assembly comprising the steps of:
(a) providing the components of:
  (i) a hub;
  (ii) a needle cannula comprising a proximal end, a distal end, and a lumen extending therebetween, said cannula is mourned to said hub;
  (iii) a housing engageable to said hub and extending distally from said hub, said housing comprising a safety shield guiding means;
  (iv) a safety shield longitudinally moveable with respect to said housing by said safety shield guiding means from a proximal position to a distal position;
  (v) a compression spring between one of said hub or said housing and said safety shield, said spring having a spring constant a free length and compressed length;
(b) identifying a first friction force between a typical patient's skin and said needle cannula;
(c) identifying a second friction force between said blood collection assembly and a patient's skin;
(d) assembling said components wherein said shield has a proximal position, an intermediate position, and a fully extended distal position in relation to said housing;
(e) providing a spring constant and spring length combination suitable for said spring to exert a force on said safety shield tat is in equilibrium with said first and second friction forces while said distal end of said cannula is percutaneously inserted into a patient's skin and said safety shield is in said intermediate position.

What is claimed is:

1. A shieldable needle assembly comprising:
a needle cannula having a proximal end and a distal end;
a hub mounted to said needle cannula at a location spaced from said distal end of said needle cannula;
a substantially tubular housing at least a portion of which projects distally from said hub toward said distal end of said needle cannula;
a safety shield telescoped over said needle cannula and having at least a portion slidably disposed between said needle cannula and said housing, said safety shield being releasably retained in a proximal position where said safety shield is spaced from said distal end of said needle cannula, said safety shield being movable from said proximal position to a distal position where said safety shield surrounds portions of said needle cannula distally of said housing;
a spring for propelling said safety shield from said proximal position to said distal position, upon release of said safety shield; and
an actuator slidably mounted to said hub, said actuator being movable distally relative to said hub and said safety shield, a portion of said actuator being configured for releasing said safety shield, such that said spring element is able to propel said safety shield toward said distal position.

2. The needle assembly of claim 1, wherein one of said housing and said safety shield includes a latch, and wherein the other of said housing and said safety shield includes a detent for releasably engaging the latch and for releasably holding said safety shield in said proximal position.

3. The needle assembly of claim 2, wherein said actuator comprises a proximal end extending proximally from said hub and a distal end substantially aligned with said latch, such that said a portion of said actuator being configured for releasing said safety shield said latch from said detent in response to said movement of said actuator.

4. The needle assembly of claim 3, wherein said actuator includes a portion disposed externally of said housing for permitting manual actuation.

5. The needle assembly of claim 3, wherein said proximal end of said housing is capable of being engaged with a detachable holder useful for receiving collection containers.

6. The needle assembly of claim 5, wherein said proximal end of said actuator is movable in the distal direction by insertion of a collection container into the proximal end of said holder.

7. The needle assembly of claim 2, wherein said housing includes a latch recess, said latch being on said safety shield and being engageable with said latch recess of said housing when said safety shield is in said distal position for preventing further distal movement of said safety shield from said distal position and for preventing a return proximal movement of said safety shield from said distal position.

8. The needle assembly of claim 1, wherein the safety shield is substantially tubular and is spaced radially outwardly from said needle cannula, said spring element being a coil spring surrounding said needle cannula and engaged with said tubular safety shield.

9. The needle assembly of claim 8, wherein said coil spring exerts a spring force of 0.02–0.20 pounds between said safety shield and one of said hub or said housing while said safety shield is in the proximal position.

10. The needle assembly of claim 1, wherein said housing includes at least one non-cylindrical external region for digital gripping of said housing.

11. The needle assembly of claim 10, wherein said distal end of said needle cannula is beveled to a point, said bevel being oriented with respect to non-cylindrical region of said housing.

12. The needle assembly of claim 10, wherein said non-cylindrical region includes a pair of opposed flats extending longitudinally along portions of said housing on opposite respective sides of said housing, said flats each including at least one surface irregularity for facilitating gripping.

13. The needle assembly of claim 1, further comprising a distal packaging cap removably disposed over said distal end of said needle cannula.

14. The needle assembly of claim 1, wherein said housing is formed from a transparent plastic material.

15. The needle assembly of claim 1, wherein said safety shield includes indicia for providing visual indications of movement of said shield relative to said housing.

16. The needle assembly of claim 15, wherein said distal end of said needle cannula is beveled to a point, said indicia on said shield being aligned with said bevel.

17. A blood collection assembly comprising:
a substantially cylindrical holder having an open proximal end, a distal end and a tubular sidewall extending between said ends, said tubular sidewall being configured for possible insertion of a collection container, an end wall at said distal end of said holder, said end wall having a aperture with needle mounting structure formed thereon; and
a needle assembly comprising
a needle cannula having a pointed proximal end and a pointed distal end thereof,
a hub mounted to said needle cannula between said pointed proximal end and said pointed distal end thereof
a housing spaced radially outwardly from said needle cannula and projecting distally from said distal end of said hub to a location spaced proximally from said distal end of said needle cannula,
a safety shield surrounding said needle cannula and having at least a portion disposed between said needle cannula and said housing, said safety shield being releasably retained in a proximal position such that said safety shield is disposed proximally of said distal end of said needle cannula, said safety shield being movable to a distal position where said safety shield encloses said pointed distal end of said needle cannula,
a spring for propelling said safety shield from said proximal position to said distal position, and
an actuator slidably mounted to said hub, said actuator being movable distally relative to said hub and said safety shield, a portion of said actuator being configured for releasing said safety shield, such that said spring element is able to propel said safety shield toward said distal position.

18. The blood collection assembly of claim 17 wherein said housing includes a detent, and wherein said safety shield includes a latch for releasably retaining said safety shield in said proximal position.

19. The blood collection assembly of claim 18, wherein said actuator including a proximal end disposed within said needle holder and a distal end disposed substantially adjacent said latch of said safety shield, said proximal end of said actuator being engageable by a collection container for urging said actuator distally and into a position for disengaging said latch from said detent on said housing.

20. The blood collection assembly of claim 17, wherein said actuator includes a actuator button disposed externally of said holder and said needle assembly for permitting manual actuation of said safety shield.

21. The blood collection assembly of claim 18, wherein said actuator includes an actuator button disposed externally of said holder and a proximal end extending into said holder, said actuator including a distal end disposed adjacent said latch of said safety shield, wherein distal movement of said actuator is moveable by either insertion of a collection container into said proximal end of said holder or manual movement of said actuator button.

22. The blood collection assembly of claim 17, wherein said safety shield is substantially tubular and includes a sidewall spaced outwardly from said needle cannula, said spring element being a coil spring surrounding said needle and engaged with said tubular safety shield.

23. The blood collection assembly of claim 17, wherein said holder includes a flange projecting outwardly at said proximal end, said flange including a flat edge aligned substantially perpendicular to a plane passing symmetrically through said distal end of said needle cannula.

24. The blood collection assembly of claim 23, wherein said pointed distal end of said cannula comprises a bevel oriented to said flange of said holder.

25. The blood collection assembly of claim 17, wherein said housing is formed from a transparent material.

26. The blood collection assembly of claim 17, wherein said safety shield is formed with indicia for providing visible indication of movement of said safety shield relative to said housing.

27. A method of making a blood collection assembly comprising the steps of:
(a) providing the components of:
(i) a hub;
(ii) a needle cannula comprising a proximal end, a distal end, and a lumen extending therebetween, said cannula is being mounted to said hub;
(iii) a housing engageable to said hub and extending distally from said hub, said housing comprising a safety guide;
(iv) a safety shield longitudinally moveable with respect to said housing by said safety shield guide from a proximal position to a distal position at which the distal end of said cannula is fully covered;
(v) a compression spring between one of said hub or said housing and said safety shield, said spring configured to move said safety shield from the proximal position, to an intermediate position, and further to the fully extended distal position;
(vi) an actuator slidably mounted to said hub, said actuator being movable distally relative to said hub and said safety shield, a portion of said actuator being configured for releasing said safety shield, such that said spring element is able to propel said safety shield toward said distal position; and
(b) assembling said components,
wherein said spring exerts sufficient force to move said safety shield to said distal position without exerting enough force to rush said needle cannula out of a patient into which said cannula has been inserted while said safety shield is in said intermediate position.

28. The method of making a blood collection assembly of claim 27, wherein said safety shield guide comprises a channel.

* * * * *